United States Patent
Steinmetz et al.

(10) Patent No.: US 11,739,301 B2
(45) Date of Patent: Aug. 29, 2023

(54) TYMOVIRUS VIRUS AND VIRUS-LIKE PARTICLES AS NANOCARRIERS FOR IMAGING AND THERAPEUTIC AGENTS

(71) Applicant: CASE WESTERN RESERVE UNIVERSITY, Cleveland, OH (US)

(72) Inventors: Nicole F. Steinmetz, San Diego, CA (US); Hema Masarapu, Cleveland, OH (US); He Hu, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 448 days.

(21) Appl. No.: 16/759,652

(22) PCT Filed: Oct. 29, 2018

(86) PCT No.: PCT/US2018/058031
§ 371 (c)(1),
(2) Date: Apr. 27, 2020

(87) PCT Pub. No.: WO2019/084555
PCT Pub. Date: May 2, 2019

(65) Prior Publication Data
US 2020/0283738 A1    Sep. 10, 2020

Related U.S. Application Data

(60) Provisional application No. 62/577,882, filed on Oct. 27, 2017.

(51) Int. Cl.
*C12N 7/00* (2006.01)
*A61K 47/54* (2017.01)
*A61K 47/55* (2017.01)
*A61P 35/00* (2006.01)
*A61K 31/136* (2006.01)
*A61K 31/704* (2006.01)
*A61K 41/00* (2020.01)

(52) U.S. Cl.
CPC ............. *C12N 7/00* (2013.01); *A61K 47/546* (2017.08); *A61K 47/55* (2017.08); *A61P 35/00* (2018.01); *A61K 31/136* (2013.01); *A61K 31/704* (2013.01); *A61K 41/0071* (2013.01)

(58) Field of Classification Search
None
See application file for complete search history.

(56) References Cited

U.S. PATENT DOCUMENTS

| | | |
|---|---|---|
| 5,004,606 A | 4/1991 | Frincke |
| 9,925,281 B2 | 3/2018 | Steinmetz et al. |
| 10,086,095 B2 | 10/2018 | Steinmetz et al. |
| 10,207,014 B2 | 2/2019 | Steinmetz et al. |
| 10,478,510 B2 | 11/2019 | Steinmetz |
| 11,020,497 B2 | 6/2021 | Steinmetz et al. |
| 11,167,047 B2 | 11/2021 | Steinmetz et al. |
| 2005/0019270 A1 | 1/2005 | Finlay et al. |
| 2005/0266020 A1 | 12/2005 | Boehm et al. |
| 2006/0216238 A1 | 9/2006 | Manchester et al. |
| 2007/0248617 A1 | 10/2007 | Bachmann et al. |
| 2007/0258889 A1 | 11/2007 | Douglas et al. |
| 2007/0284545 A1 | 12/2007 | Isacsson et al. |
| 2010/0183504 A1 | 7/2010 | Chen |
| 2015/0033418 A1 | 1/2015 | Lommel et al. |
| 2015/0265696 A1 | 9/2015 | Gourapura et al. |
| 2017/0216438 A1 | 8/2017 | Steinmetz |
| 2020/0179468 A1 | 6/2020 | Steinmetz |
| 2022/0211881 A1 | 7/2022 | Steinmetz |

FOREIGN PATENT DOCUMENTS

| | | |
|---|---|---|
| EP | 2316480 A1 | 5/2011 |
| JP | 2009524699 A | 7/2009 |
| WO | 01/18199 A1 | 3/2001 |
| WO | 200118199 A1 | 3/2001 |
| WO | 2001/0026682 A2 | 4/2001 |
| WO | 2003092623 A2 | 11/2003 |
| WO | 2012078069 A1 | 6/2012 |
| WO | 2013181557 A1 | 12/2013 |
| WO | 2015/0039255 A1 | 3/2015 |
| WO | 2015/188110 A1 | 12/2015 |
| WO | 2016019393 A1 | 2/2016 |
| WO | 2016/073972 A1 | 5/2016 |
| WO | 2016073972 A1 | 5/2016 |
| WO | 2016/149264 A1 | 9/2016 |
| WO | 2017/004123 A1 | 1/2017 |

OTHER PUBLICATIONS

Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Applicant: Case Western Reserve University; "Cancer Immunotherapy Using Virus Particles"; European Patent Application No. 21201960.8; Extended European Search Report dated Jan. 19, 2022; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Gonzalez Maria Jet al: "Interaction of Cowpea Mosaic Virus (CPMV) Nanoparticles with Antigen Presenting Cells In Vitro and In Vivo", PLOS One, vol. 4, No. 11, Nov. 2009 (Nov. 2009), XP002780311, ISSN: 1932-6203.

(Continued)

*Primary Examiner* — Nicole Kinsey White
(74) *Attorney, Agent, or Firm* — Tarolli, Sundheim, Covell & Tummino, LLP

(57) ABSTRACT

A method of targeting cancer tissue in a subject includes administering to the subject a plurality of functionalized Tymovirus virus or virus-like particles loaded with or conjugated to an imaging agent, a therapeutic agent or a targeting agent.

28 Claims, 13 Drawing Sheets

(56) References Cited

OTHER PUBLICATIONS

Patrick h. Lizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Saunders K et al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Office action for Japanese Patent Application No. 2017-524349, dated Jan. 31, 2020.
Yildiz et al., "Applications of viral nanoparticles in medicine", Current Opinion in Biotechnology, vol. 22, Issue 6, pp. 901-908.
Aljabali, et al., "CPMV-DOX Delivers", Molecular Pharmaceutics, 2013, 10, pp. 3-10.
Wen, et al., "Interior Engineering of a Viral Nanoparticle and its Tumor Homing Properties" Macromolecules, vol. 13, No. 12, Dec. 2012.
Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.
Brennan, et al., "Cowpea Mosaic Virus as a Vaccine Carrier of Heterologous Antigens", Molecular Biotechnology, vol. 17, No. 1, Jan. 2001.
Gonzalez, et al., "Interaction of Cowpea Mosaic Virus (CPMV) Nanoparticles with Antigen Presenting Cells in Vitro and In Vivo", PLOS One, vol. 4, No. 11, Nov. 2009.
Lizotte, et al., "Plant-derived viral-like nanoparticle immunotherapy suppress development of metastatic lung cancer", Journal of Immunology, vol. 194, Issue 1 Supplement, May 2015.
Patrick H. Lizotte, "Novel approaches to targeting innate immunity for cancer immunotherapy", Proquest Dissertations Publishing, May 2015.
Supplementary European Search Report for Patent Application No. 15857504.3-1111/3215520, dated May 28, 2018.
International Search Report for Application No. PCT/US15/59675.
Plchova et al. Expression of Human papillomavirus 16 E7ggg oncoprotein on N- and C-terminus of Potato virus X coat protein in bacterial and plant cells. Protein Expression and Purification 77 (2011) 146-152.
Applicant: Case Western Reserve University; "Cancer Immunotherapy Using Virus Particles"; European Patent Application No. 18764856.3 for Supplementary European Search Report dated Dec. 22, 2020; 8 pgs.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Applicant: Case Western Reserve University; "Cancer Immunotherapy Using Virus Particles"; Office Action, dated Aug. 4, 2020; 3 pgs.
Applicant: Case Western Reserve University; "Plant Virus Particles for Delivery of Antimitotic Agents"; Extended European Search Report; dated Aug. 17, 2020; 11 pgs.
"CWRU researcher to turn plant virus shells against human cancers", The Daily, CWRU Researcher to Turn Plant Virus Shells Against Human Cancers. Case Western Reserve University, Apr. 18, 2016.

Alaa A. Al. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Applicant: Case Western Reserve University; "Cancer Immunotherapy Using Virus Particles"; Canadian Office Action, dated Aug. 4, 2020; 3 pgs.
Applicant: Case Western Reserve University; "Plant Virus Particles for Delivery of Antimitotic Agents"; Extended European Search Report; dated Aug. 25, 2020; 11 pgs.
Canan Uluog, et al.: "Intermediate dose of methotrexate toxicity in non-Hodgkin lymphoma", General Pharmacology, vol. 32, 1999, pp. 215-218, XP55711259.
Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.
European Search Report for Patent Application No. 15857504.3-1111/3215520, dated May 7, 2018.
Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
International Search Report for Application No. PCT/US15/59675 (dated 2016).
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.
Lee et al. "Biodegradable Viral Nanoparticle/Polymer Implants Prepared via Melt-Processing", ACS Nano ePub Sep. 13, 2017 vol. 11 No 9 pp. 8777-8780.
Lee et al., "PEGylation to Improve Protein Stability During Melt Processing", Macromol Biosci 1-43, 57-75, Oct. 2015 vol. 15 No 10 pp. 1332-1337.
Lizotte, et al., "Plant-derived viral-like nanoparticle immunotherapy suppress development of metastatic lung cancer", Journal of Immunology, vol. 194, Issue 1 Supplement, May 2015; 4 pgs.
Matsuura et al. Self-assembly of Ni-NT A-modified [3-annulus peptides into artificial viral capsids and encapsulation of His-tagged proteins. Org Biomol. Chem., 2016, 14, 7869. DOI: 10.1039/c6ob01227b (Year: 2016).
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Nicole F. Steinmetz; U.S. Appl. No. 16/347,503, filed May 3, 2019; NonFinal Rejection dated Jun. 15, 2022; 36 pgs.
Nicole F. Steinmetz; U.S. Appl. No. 16/614,676, filed Nov. 18, 2019; NonFinal Rejection dated Jun. 3, 2022; 28 pgs.
Office action for Chinese Patent Application No. 201580063662.6, dated Mar. 4, 2020.
Office action for European Patent Application No. 15 857 504.3-1111, dated Mar. 18, 2020.
Office action for Japanese Patent Application No. 2017-524349, drafted Jan. 31, 2020; dated Feb. 10, 2020; 6 pgs.
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Plchova et al. Expression of Human papillomavirus 16 E7ggg oncoprotein on N- and C-terminus of Potato virus X coat protein in bacterial and plant cells. Protein Expression and Purification 77 (2011); p. 146-152.
Sheen et al., "Stimulating Antitumor Immunity with Nanoparticles", Wiley Interdiscip Rev Nanomed Nanobiotechnol, Oct. 2014, vol. 6, pp. 496-505.
Smyth etal. Treatment of rapidly growing K-BALB and CT26 mouse tumours using Semliki Forest virus and its derived vector. Gene Therapy (2005) 12, 147-159.

(56) References Cited

OTHER PUBLICATIONS

Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Wen et al. Design of virus-based nanomaterials for medicine, biotechnology, and energy. Chem. Soc. Rev., 2016, 45, 4074. DOI: 10.1039/c5cs00287g (Year: 2016).
Yildiz, et al., "Applications of viral nanoparticles in medicine", Current Opinion in Biotechnology, vol. 22, Issue 6, (2011); pp. 901-908.
Chinese Patent Appl. No. 201580063662.6; Chinese Office Action; dated May 5, 2022; 3 pgs.
Czapar, Anna et al. Tobacco Mosaic Virus Delivery of Phenanthriplatin for Cancer therapy. American Chemical Society. Nano 2016 (10) pp. 4119-4126 (Year: 2016).
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).
Le, Duc et al. Chemical addressability of potoato virus X for its applications in bio/nanotechnology. El Sevier. Journal of Structural Biology 200 (2017). pp. 360-368. (Year: 2017).
Le, Duc et al. Potato virus X, a filamentous plant viral nanoparticle for doxorubicin delivery in cancer therapy. Royal Society of Chemistry. Nanoscale, 2017 (9). pp. 2348-2357. (Year: 2017).
Nicole F. Steinmetz, U.S. Appl. No. 16/998,210, filed Aug. 7, 2020; Non-Final OA dated Dec. 7, 2022.
Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).
Bruckman et al. (Nano Letters. Mar. 2014; 14: 1551-1558).
Imamura et al. ("FOXA 1 promotes tumor progression in prostate cancer via the insulin-like growth factor binding protein 3 pathway." (2012)).
Lam, et al. (WIREs Nanomed Nanobiotechnol Jan./Feb. 2018 vol. 10: 1-18).
Mitoxantrone. Drug Bank Online. Website. https://go.drugbank.com/drugs/DB01204. (Accessed Dec. 15, 2022) (Year: 2022).
Mosquera et al. (Acc. Chem. Res. 2018, 51, 9, 2305-2313 Publication Date: Aug. 29, 2018.
Nicole F.Steinmetz; U.S. Appl. No. 16/597,509, filed Oct. 9, 2019; Non-Final Office Action, dated Dec. 27, 2022; 12 pgs.
Nicole F.Steinmetz; U.S. Appl. No. 17/129,463, filed Dec. 21, 2020; Non-Final Office Action, dated Dec. 8, 2022; 32 pgs.
Nicole F.Steinmetz; U.S. Appl. No. 17/522,182, filed Nov. 9, 2021; Non-Final Office Action, dated Jan. 5, 2023; 27 pgs.
Nicole F.Steinmetz; U.S. Appl. No. 17/677,147, filed Feb. 22, 2022; Non-Final Office Action, dated Jan. 13, 2023; 22 pgs.
Pellico et al. (Contrast Media and Molecular Imaging. 2019; Article ID 1845637: 1-13).
Pretto et al. ("Versatile reversible cross-linking strategy to stabilize CCMV virus like particles for efficient siRNA delivery." Bioconjugate chemistry 30.12 (2019): 3069-3077).
Royston et al. (Journal of Colloidal and Interface Science. 2009; 332: 402-407).
Tamoxifen. Drug Bank Online. Website. https://go.drugbank.com/drugs/DB00675. (Accessed: Dec. 15, 2022) (Year: 2022).
Temming et al. (bioconjugate Chemistry. 2006; 17: 1385-1394).
Xiao et al. (International Journal of Molecular Medicine. 2016; 38: 1319-326).
Zhang et al. (Theranostics. 2018; 8 (9): 2521-2548).

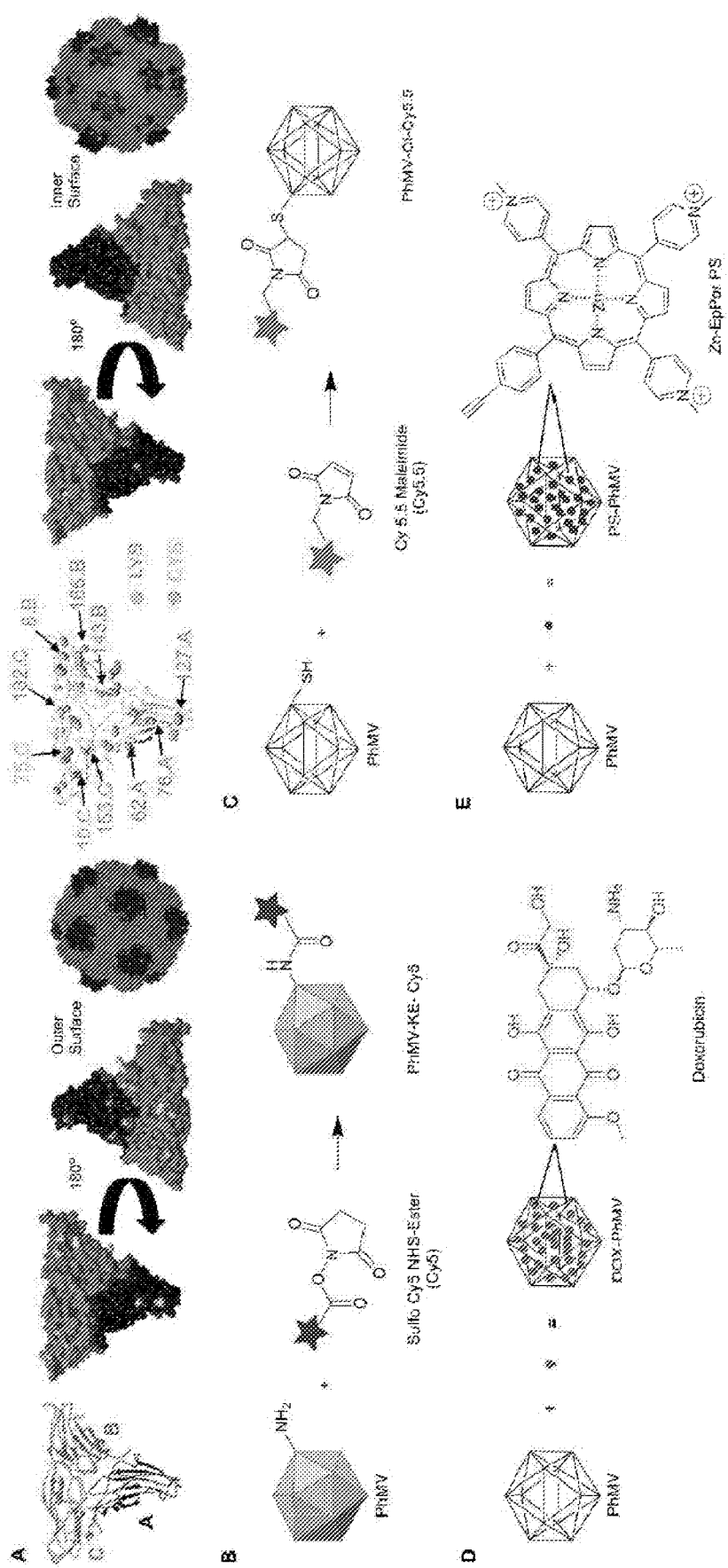
Figs. 1A-E

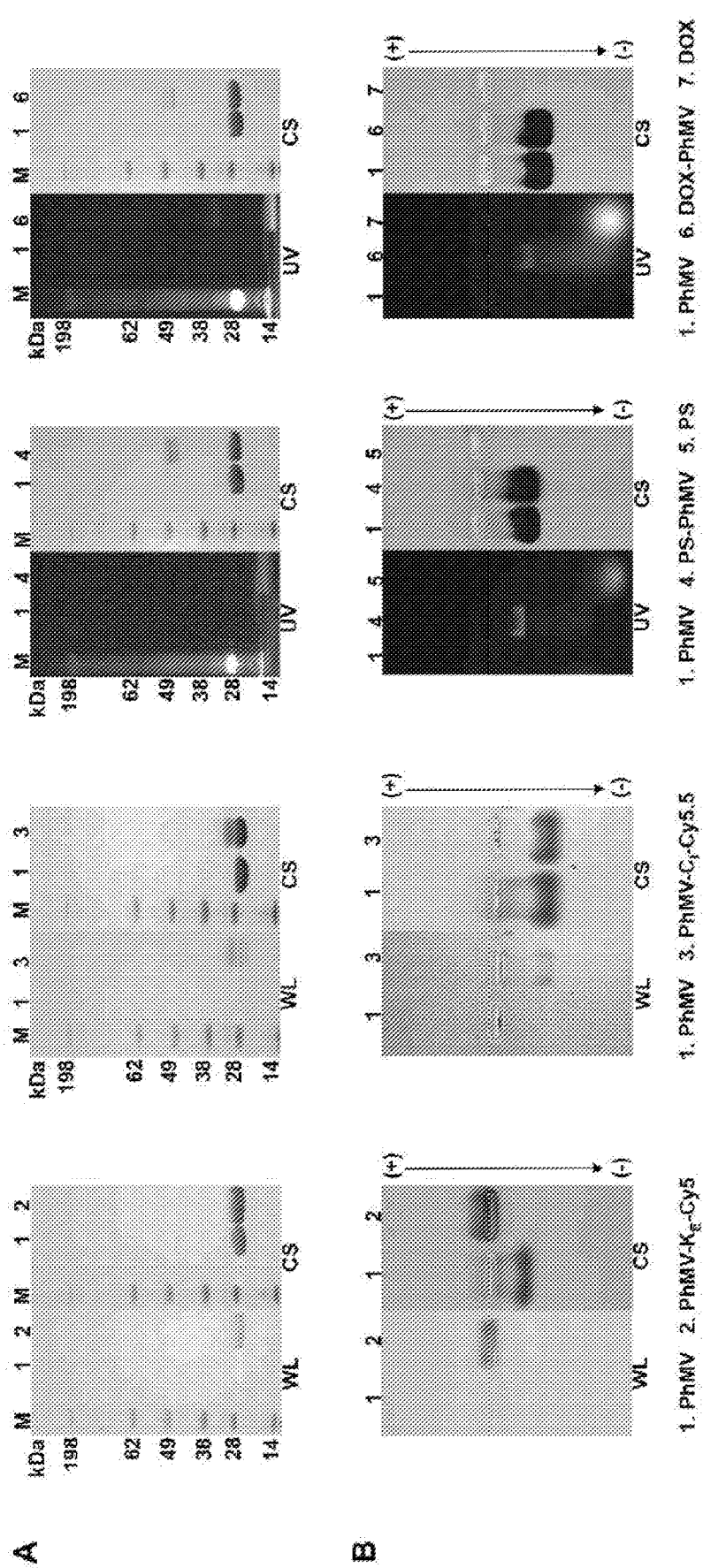
Figs. 2A-B

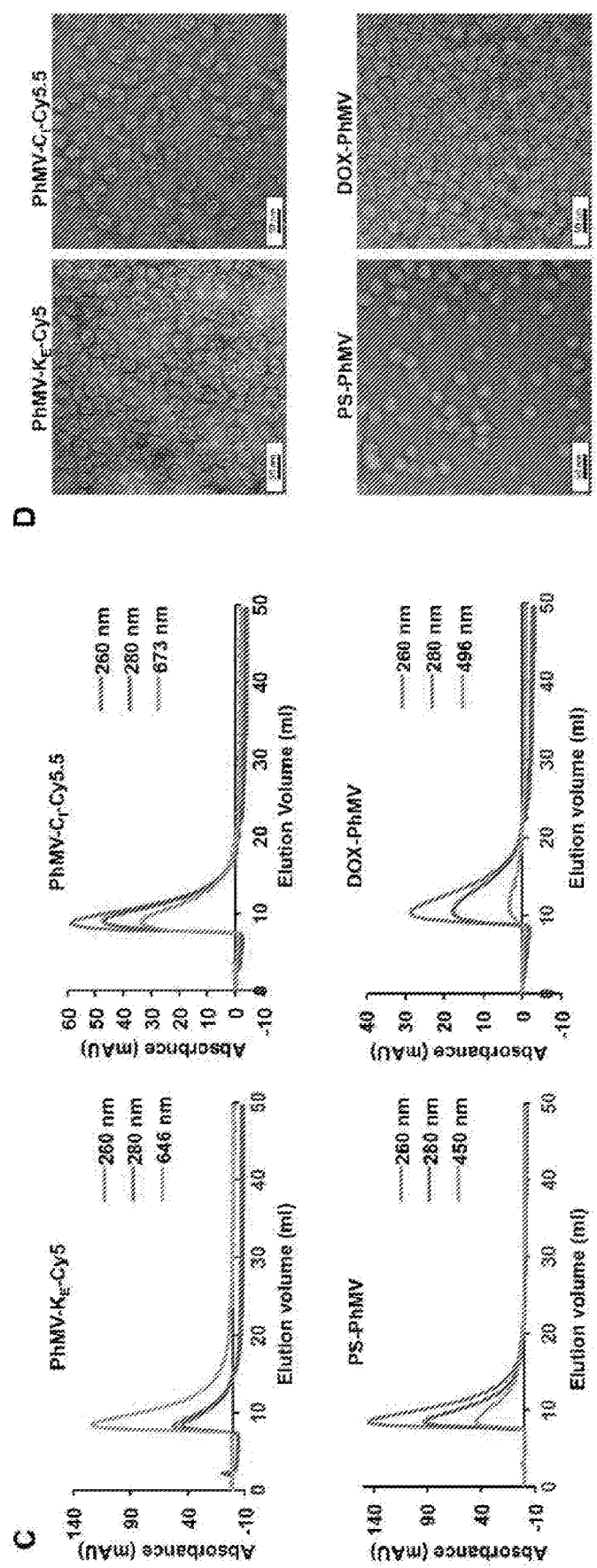
Figs. 2C-D

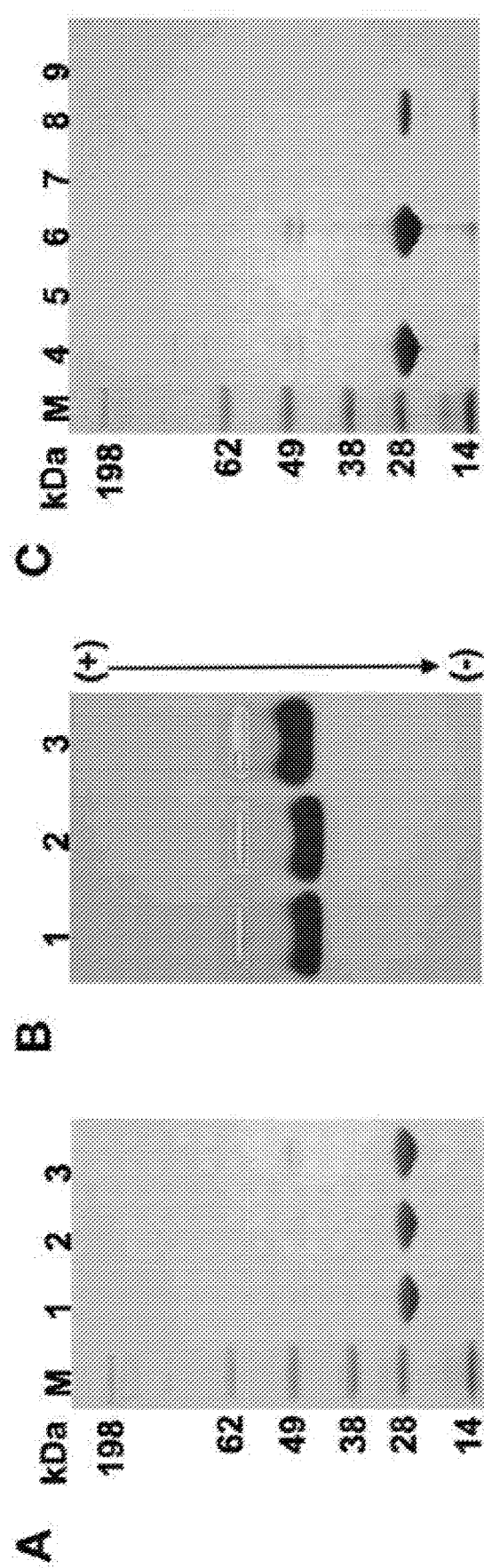
Figs. 3A-C

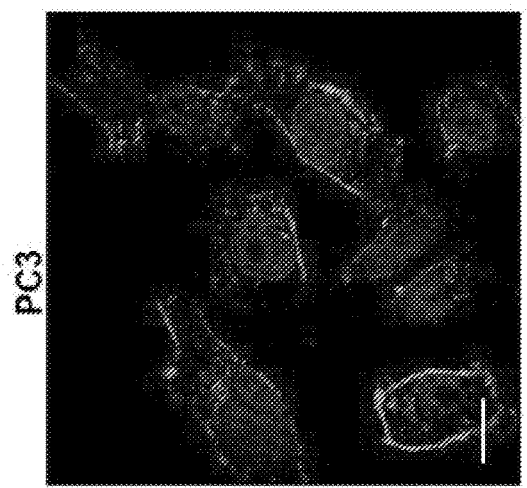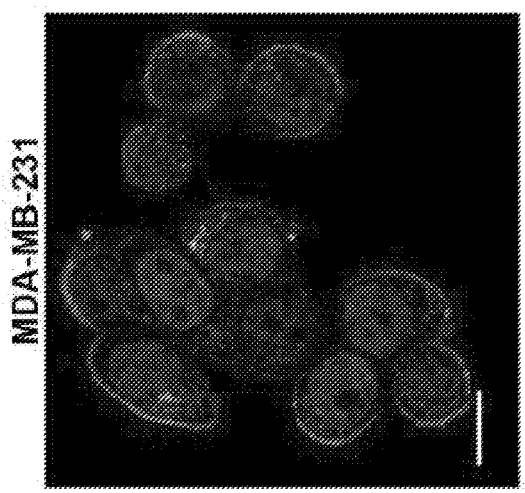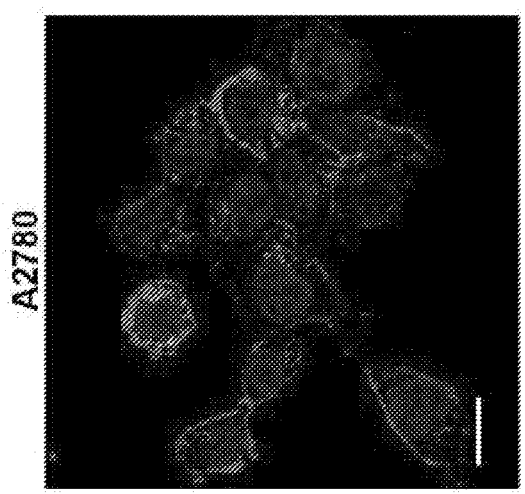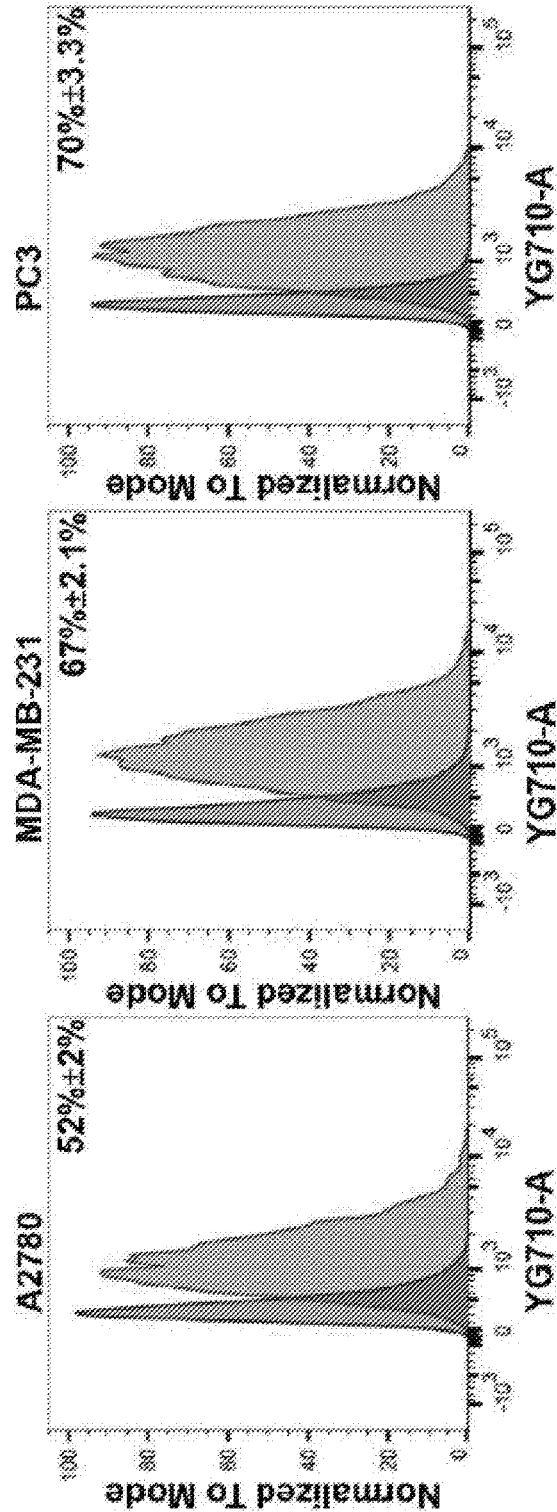
Figs. 4A-B

TYMOVIRUS VIRUS AND VIRUS-LIKE PARTICLES AS NANOCARRIERS FOR IMAGING AND THERAPEUTIC AGENTS

RELATED APPLICATION

This application claims priority from U.S. Provisional Application No. 62/577,882, filed Oct. 27, 2017, the subject matter of which is incorporated herein by reference in its entirety.

GOVERNMENT FUNDING

This invention was made with government support under Grant Nos. R01-CA202814 awarded by The National Institutes of Health (NIH) and the National Science Foundation (NSF). The United States government has certain rights in the invention.

TECHNICAL FIELD

This application relates to methods and compositions for targeting cancer tissue in a subject and/or treating cancer in a subject identified as having cancer.

BACKGROUND

Nanocarrier platforms based on natural biological building blocks offer new opportunities in the biomedical and materials sciences. Viral nanoparticles (VNPs) are self-assembling supramolecular systems that can be used to develop bioinspired nanomaterials and nanocarriers due to their simple and inexpensive production, well-defined structural features, unique shapes and sizes, genetic programmability, and robust chemistries. VNPs based on plant viruses are particularly advantageous in medicine because they are biocompatible and biodegradable, but do not infect humans and other mammals. They can carry drugs, imaging agents, and other nanoparticles in their internal cavity by assembly, infusion, or internal surface modification, and the external surface can be chemically or genetically engineered to attach targeting ligands for tissue-specific delivery. Plant VNPs have already overcome many of the challenges of nanoparticle delivery, such as low stability in biological fluids, efficient delivery across membranes, avoidance of exocytosis, and targeting specificity. We and several others have established a broad range of plant VNPs such as those based on Cowpea mosaic virus (CPMV), Cowpea chlorotic mottle virus (CCMV), Brome mosaic virus (BMV), Potato virus X (PVX) and Tobacco mosaic virus (TMV).

Virus-like particles (VLPs) are a subset of VNPs, which lack the viral genome and assemble spontaneously from virus structural proteins into noninfectious protein cage-like structures. Many different virus structural proteins form VLPs when expressed in standard heterologous expression systems such as *Escherichia coli*, yeast, plants, mammalian cells, and insect cells. Such VLPs tend to be structurally and morphologically similar to the wildtype virus particles formed in vitro and demonstrate similar cell tropism, uptake, and intracellular trafficking.

SUMMARY

Embodiments described herein relate to a method of targeting cancer tissue in subject. The method includes administering to the subject a plurality of functionalized Tymovirus virus or Tymovirus virus-like particles (VLPs). The Tymovirus virus or VLPs can be administered to the subject at an effective amount. The Tymovirus virus can belong to the physalis mottle virus (PhMV) species. The Tymovirus virus or VLPs are loaded with or conjugated to one or more of a therapeutic agent, an imaging agent, or a targeting agent. The targeted cancer tissue can include prostate, breast or ovarian cancer tissue. In some embodiments, the Tymovirus virus or VLPs have been PEGylated.

In some embodiments, the Tymovirus virus or VLPs include an imaging agent. The imaging agent can include a fluorescent molecule for fluorescent imaging or a chelated metal. In some embodiments, the method can further include the step of imaging cancer tissue in the subject using an imaging device subsequent to administering the Tymovirus virus or VLPs.

In some embodiments, the Tymovirus virus or VLPs include a therapeutic agent (e.g., a cytotoxic compound). The therapeutic agent can include an antitumor agent such as doxorubicin or mitoxantrone. In some embodiments, the therapeutic agent can include a photodynamic therapeutic (PDT) photosensitizer agent. The PDT agent can be selected from a porphyrin or a mettalloporphyrin compound. In certain embodiments, the PDT agent is a cationic zinc ethynylphenyl porphyrin.

In some embodiments, the one or more of a therapeutic agent, an imaging agent, or a targeting agent is directly conjugated to the Tymovirus virus or VLPs. In some embodiments, the one or more of a therapeutic agent, an imaging agent, or a targeting agent is conjugated to the Tymovirus virus or VLPs particles via a linker.

In some embodiments, the Tymovirus virus or VLPs include multiple targeting agents. The spacing and location of the targeting agents on the Tymovirus virus or VLPs can be controlled to facilitate delivery, targeting, and/or therapeutic efficacy of the Tymovirus virus or VLPs when administered to a subject.

Other embodiments described herein relate to a method of treating cancer in a subject in need thereof. The method includes administering to the subject a therapeutically effective amount of a plurality of functionalized Tymovirus virus or VLPs loaded with or conjugated to one or more therapeutic agents. The Tymovirus virus or VLPs can be administered together with a pharmaceutically acceptable carrier. The cancer treated can include prostate, breast or ovarian cancer. The Tymovirus virus can belong to the physalis mottle virus (PhMV) species. In some embodiments, the Tymovirus virus or VLPs have been PEGylated.

In some embodiments, the therapeutic agent includes a cytotoxic compound. The cytotoxic compound can include an antitumor agent such as doxorubicin or mitoxantrone.

In some embodiments, the therapeutic agent includes a photodynamic therapeutic (PDT) photosensitizer agent. The PDT agent can be selected from a porphyrin or a mettalloporphyrin compound. In certain embodiments, the PDT agent is a cationic zinc ethynylphenyl porphyrin.

In some embodiments, the Tymovirus virus or VLPs further include one or more targeting agents. In some embodiments, the targeting agents can be conjugated to the Tymovirus virus or VLPs. The targeting agents can be directly conjugated to the Tymovirus virus or VLPs or conjugated to the Tymovirus virus or VLPs via a linker.

In some embodiments, the Tymovirus virus or VLPs include multiple targeting agents. The spacing and location of the targeting agents on the Tymovirus virus or VLPs can be controlled to facilitate delivery, targeting, and/or therapeutic efficacy of the Tymovirus virus or VLPs when administered to a subject.

Another embodiment described herein relate to a method of detecting cancer in a subject. The method includes administering to the subject a plurality of functionalized Tymovirus virus or Tymovirus virus-like particles (VLPs) that have been loaded with or conjugated to an imaging agent. The method also includes detecting the imaging agent in the subject using an imaging device subsequent to administering the Tymovirus virus or VLPs to determine the location and/or distribution of the cancer in the subject. The Tymovirus virus or VLPs can be administered together with a pharmaceutically acceptable carrier.

The detected cancer can include breast cancer, ovarian cancer, or prostate cancer. The Tymovirus virus can belong to the physalis mottle virus (PhMV) species. In some embodiments, the Tymovirus virus or VLPs have been PEGylated.

In some embodiments, the imaging agent can include a fluorescent molecule for fluorescent imaging or a chelated metal for MRI imaging.

In some embodiments, the Tymovirus virus or VLPs further include one or more targeting agents. In some embodiments, the targeting agents can be conjugated to the Tymovirus virus or VLPs. The targeting agents can be directly conjugated to Tymovirus virus or VLPs or conjugated to the Tymovirus virus or VLPs via a linker.

In some embodiments, the Tymovirus virus or VLPs include multiple targeting agents. The spacing and location of the targeting agents on the Tymovirus virus or VLPs can be controlled to facilitate delivery, targeting, and/or therapeutic efficacy of the Tymovirus virus or VLPs when administered to a subject.

Other embodiments described herein relate to a functionalized Tymovirus based nanoparticle. The nanoparticle includes a Tymovirus virus or Tymovirus virus-like particle (VLP) that has been loaded with or conjugated to one or more of an imaging agent, a therapeutic agent, or a targeting agent. The Tymovirus virus can belong to the physalis mottle virus (PhMV) species. In some embodiments, the Tymovirus virus or VLP has been PEGylated.

In some embodiments, the imaging agent, the therapeutic agent, or the targeting agent is conjugated directly or indirectly to the interior of the Tymovirus virus or VLP. In some embodiments, the imaging agent, the therapeutic agent, or the targeting agent is conjugated directly or indirectly via a linker to the exterior of the Tymovirus virus or VLP. In other embodiments, the imaging agent, the photodynamic therapeutic (PDT) photosensitizer agent or the cytotoxic compound is non-covalently infused into the interior of the Tymovirus virus or VLP.

In some embodiments, the Tymovirus virus or VLP includes an imaging agent. The imaging agent can include a fluorescent molecule for fluorescent imaging or a chelated metal for MRI imaging.

In some embodiments, the Tymovirus virus or VLP includes a therapeutic agent, such as a cytotoxic compound. The therapeutic agent can include an antitumor agent such as doxorubicin or mitoxantrone.

In some embodiments, the therapeutic agent includes a photodynamic therapeutic (PDT) photosensitizer agent. The PDT agent can be selected from a porphyrin or a mettalloporphyrin compound. In certain embodiments, the PDT agent is a cationic zinc ethynylphenyl porphyrin.

BRIEF DESCRIPTION OF THE DRAWINGS

FIGS. 1(A-E) illustrate a structure of PhMV and strategies used for the functionalization of PhMV-derived VLPs. (A) Ribbon diagram of the PhMV VLP icosahedral asymmetric unit consisting of A, B and C subunits. Five A subunits make up pentameric capsomeres at the icosahedral 5-fold axes, while B and C subunits form hexamers at the icosahedral 3fold axes. Representation of internal and external surfaces (with 180-degree rotation) of the PhMV asymmetric unit, highlighting surface-exposed (K62, K143, K153 and K166) and buried (K8, K10, K76, K182 and K127) lysine residues (blue), and the single cysteine residue (C75, green). PhMV forms from 180 identical coat protein subunits arranged in a T=3 icosahedral structure. Images created using UCSF Chimera (PDB: 1E57). The capsid is characterized by prominent protrusions of pentamers and hexamers. (B) Schematic of PhMV labeling with sulfo-Cy5 NHS ester using lysine-NHS ester chemistry. (C) Conjugation of Cy5.5-maleimide to internal cysteine residues using maleimide-thiol chemistry. (D) DOX infusion into PhMV, leading to cargo-loaded particles. Washing and ultracentrifugation is used to remove excess DOX, yielding intact PhMV with infused DOX (DOX-PhMV). (E) Schematic of PS (blue) loading into PhMV via infusion, yielding PS-PhMV particles.

FIGS. 2(A-D) illustrate characterization of fluorophore-labeled and drug-loaded VLPs. (A) SDS-PAGE analysis of PhMV-KECyS, PhMV-CI-Cy5.5, PS-PhMV, and DOX-PhMV visualized under UV light (UV), white light (WL) before staining, and under white light after Coomassie blue staining (CS). M=SeeBlue Plus2 molecular weight (kDa) standard; 1=Native PhMV; 2=PhMV-KE-Cy5; 3=PhMV-CI-Cy5.5; 4=PS-PhMV; 5=PS; 6=DOX-PhMV; 7=DOX. (B) Agarose gel electrophoresis of PhMV-KE-Cy5, PhMV—CI-Cy5.5, PS-PhMV, and DOX-PhMV visualized under UV light and white light before, and under white light after Coomassie blue staining (CS). Functionalized particles loaded in each lane was same as described above for SDS-PAGE analysis (note: the white marks in the center of the gel are the pockets into which the samples were loaded prior to electrophoretic separation). (C) Size exclusion chromatograms of PhMV-KE-Cy5 [monitored at 260 nm (blue), 280 nm (red) and 646 nm (green, sulfo-Cy5 NHS ester absorbance], PhMV-CI-Cy5.5 [monitored at 260 nm (blue), 280 nm (red) and 673 nm (green, Cy5.5-maleimide absorbance], PS-PhMV [monitored at 260 nm (blue), 280 nm (red) and 450 nm (green, PS absorbance] and DOX-PhMV [monitored at 260 nm (blue), 280 nm (red) and 496 nm (green, DOX absorbance]. (D) Transmission electron micrographs of negatively stained (UAc) PhMV-KE-Cy5, PhMV-CI-Cy5.5, PS-PhMV, and DOX-PhMV.

PhMV was tagged with sulfo-Cy5 NHS ester (pseudo green), the cell membrane was stained with wheat germ agglutinin (WGA)-Alexa Fluor 555 (pseudo pink) and the nucleus was stained with DAPI (blue). Scale bars=25 μm (B) Flow cytometry of A2780, MDA-MB-231 and PC-3 cells following 6 h incubation with PhMV-$K_E$-Cy5 particles. Percentage of positive cells for each sample was quantified from three replicates and represented with standard deviation (±) in the corresponding cell panels. (C) Confocal imaging of A2780 and MDA-MB-231 cells showing colocalization of PhMV-$C_f$-Cy5.5 particles with the endolysosomal marker LAMP-1 after 6 h. Nuclei are shown in blue, endolysosomes are stained with mouse anti-human LAMP-1 antibody (red) and PhMV-$C_f$-Cy5.5 (pseudo green). Colocalization signals are shown in white (overlay, bottom panel). Scale bars=25 μm. (D) FACS quantification of PhMV-$C_f$-Cy5.5 uptake using A2780, MDA-MB-231, PC-3, HeLa, RAW 264.7, U87, HT1080 and NIH/3T3 cells. All samples were measured in triplicates and analyzed using FlowJo software.

Figure 5:
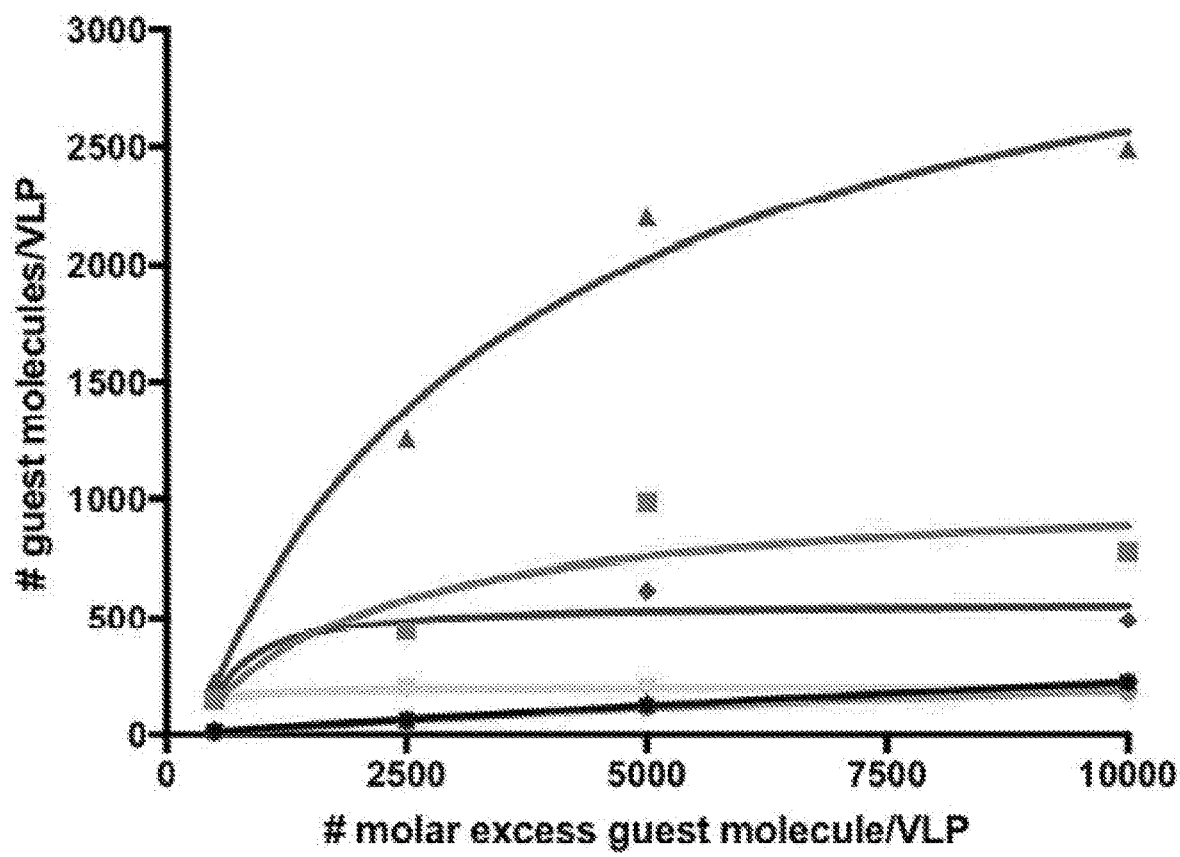
Figure 5:
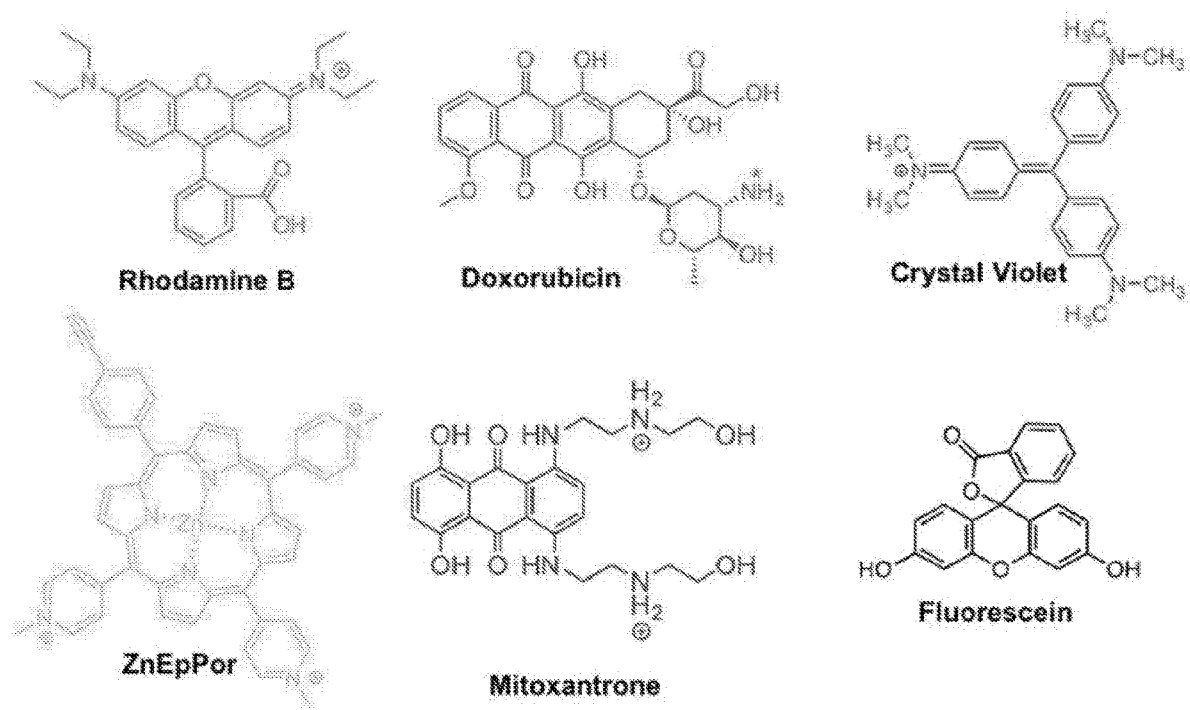

FIG. 5 illustrates the number of dye/drug (guest) molecules loaded per VLP via infusion at different molar excesses (averaged data from 2 experiments are shown). The number of guest molecules per particle was determined by UV/vis absorbance and the Bradford assay was used to determine the protein concentration. The chemical structure of each guest molecule is depicted with their respective charge. The amine group of DOX is annotated with asterisks to indicate a site of protonation (positive charge) in physiological conditions.

FIGS. 6(A-D) illustrate evaluation of cytotoxic efficacy of drug-loaded PhMV particles. (A) MTT cell viability assay of PC-3 cells using PS-PhMV. Cell viability was measured following 8 h incubation with varying concentrations of PS or PS-PhMV and 30 min illumination with white light (no cell killing was observed when cells were incubated in the dark, not shown). (B) LIVE/DEAD assay of PC-3 cells showing representative images after photodynamic therapy of cells incubated with PS-PhMV or free PS and LIVE/DEAD cell staining. Calcein-AM staining of live cells and ethidium homodimer-1 staining is shown. Scale bar=100 μm. Illuminated cells incubated with PS-PhMV showed a slight increase in cell killing efficacy ($IC_{50}$=0.03 μM) compared to free PS ($IC_{50}$=0.05 μM). Dark controls show no cytotoxicity with PS-PhMV or PS. Scale bar=100 μm. (C). Efficacy of DOX-PhMV versus DOX using A2780 (human ovarian cancer) and (D) MDA-MB-231 (human breast cancer) cells as determined by MTT assay. Cells were treated with DOX or DOX-PhMV corresponding to 0, 0.01, 0.05, 0.1, 0.5, 1, 5 and 10 μM for 24 h. $IC_{50}$ values were determined using GraphPad Prism software.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in this specification and the appended claims, the singular forms "a", "an" and "the" include plural references unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Image" or "imaging" refers to a procedure that produces a picture of an area of the body, for example, organs, bones, tissues, cells or blood.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

Prevention, as used herein, refers to any action providing a benefit to a subject at risk of being afflicted with a condition or disease such as cancer, including avoidance of the development of cancer or a decrease of one or more symptoms of the disease should cancer develop. The subject may be at risk due to exposure to a carcinogen, or as a result of family history.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Targeting," as used herein, refers to the ability of modified virus-like particles to be delivered to and preferentially accumulate in cancer tissue in a subject compared to normal tissue.

As used herein, the term "targeting agent" can refer to a molecule or molecules that are able to bind to and complex with a biomarker. The term can also refer to a functional group that serves to target or direct a nanoparticle, therapeutic agent or anti-cancer agent to a particular location, cell type, diseased tissue, or association. In general, a "targeting agent" can be directed against a biomarker.

As used herein, the term "molecular signature" can refer to a unique expression pattern of one or more biomarkers (e.g., gene(s) or protein(s)) of a cell.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

As used herein, the term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

As used herein, the term "diabodies" refers to dimeric scFvs. The components of diabodies typically have shorter peptide linkers than most scFvs and they show a preference for associating as dimers.

As used herein, the term "epitope" refers to a physical structure on a molecule that interacts with a selective component. In exemplary embodiments, epitope refers to a desired region on a target molecule that specifically interacts with a selectivity component.

As used herein, the term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

As used herein, the term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

As used herein, the term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$—$V_L$ pair.

As used herein, the term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the NH$_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility.

Embodiments described herein relate to Virus-like particles (VLPs) derived from the Tymovirus genus of plant viruses, such as physalis mottle virus (PhMV), for use as platforms for diagnostics and therapeutics by functionalizing Tymovirus based VLPs with drugs, targeting and/or imaging molecules.

The VLP platforms described herein may be engineered and tailored for desired functional applications through genetic modification, non-covalent infusion and/or bioconjugate chemistry. Protein engineering can be used to introduce new functionalities at three distinct interfaces of VLPs: internal, external, and inter-subunit. This allows the fine tuning of surface charge, drug encapsulation, ligand display, and particle stability.

In order to functionalize Tymovirus based VLPs, multiple approaches, such as bioconjugation chemistries and non covalent infusion protocols are described herein that can be used to modify the behavior and properties of the VLPs. Once functionalized, Tymovirus based VLP nanoparticles can be characterized by flow cytometry and confocal microscopy and their cytotoxic efficacy have been evaluated in human normal and ovarian, breast and prostate cancer cell lines as well as in ex vivo organ biodistribution analysis models, and in an in vivo mouse models of prostate cancer.

In one aspect, the invention provides a method of using a Tymovirus virus or Tymovirus virus-like particle (VLP) nanoparticle to target cancer tissue in a subject. The use of a Tymovirus virus or VLPs allows for nanoparticles that are biocompatible, biodegradeable, non-infectious in mammals. In addition, the Tymovirus virus or VLPs can readily be chemically engineered to carry cargo such as a therapeutic agent, an imaging agent, or a targeting agent. The method includes administering a plurality of functionalized Tymovirus virus or Tymovirus virus-like particles (VLPs) loaded with or conjugated to one or more or a therapeutic agent, an imaging agent, or a targeting agent to the subject. As defined herein, targeting cancer tissue refers to the ability of the Tymovirus virus or Tymovirus VLPs to reach and preferably accumulate within cancer tissue after being administered to the subject. The ability of Tymovirus virus or VLPs to target cancer tissue is supported by the characterization, cytotoxicity, biodistribution, tumor model studies described herein.

The Tymovirus VLPs are shown to colocalize with the endolysosomal marker LAMP-1 within about 6 hours of administration to cancer cells. While not intending to be bound by theory, it is believed that Tymovirus virus or Tymovirus VLPs are preferentially internalized by cancer cells over non-cancerous cells via endocytosis, thereby delivering the functionalized VLPs to the tumor cells at a much higher efficiency than non-transformed cells. Embodiments of the invention can deliver and internalize about 10%, about 20%, about 30%, about 40%, about 50%, about 60%, or even about 70% or more of administered externally functionalized VLPs to a subject's cancer cells. Embodiments of the invention can deliver and internalize about 10%, about 20%, about 30%, about 40%, about 50%, about 60%, about 70%, about 80%, about 90% or even about 100% of administered internally functionalized virus or VLPs to a subject's cancer cells. In specific embodiments, the Tymovirus virus or Tymovirus VLPs described herein can deliver and internalize about 95% to about 100% of administered internally functionalized Tymovirus virus or Tymovirus VLPs to cancer cells.

Tymoviruses

Embodiments described herein can include a functionalized Tymovirus virus nanoparticle. Other embodiments can relate to functionalized Tymovirus virus-like particles (VLPs) where the Tymovirus VLPs are derived from a virus of the Tymovirus genus. Tymovirus virus is a virus that primarily infects plants and has a non-enveloped icosahedral and isometric structure. The diameter of a Tymovirus, such as PhMV, is about 30 nm. Use of a Tymovirus virus or Tymovirus VLP as described herein provides the advantages of improved physical stability (e.g., after cargo loading as well as in storage) and production consistency.

A Tymovirus virus can be selected from a group consisting of Physalis Mottle Virus (PhMV), *Belladonna* Mottle Virus, Turnip Yellow Mosaic Virus, Cacao Yellow Mosaic Virus, Clitoria Yellow Vein Virus, *Desmodium* Yellow Mottle Virus, Eggplant Mosiac Virus and Passion Fruit Yellow Mosaic Virus. A comparison of coat protein sequence of PhMV with other tymoviruses revealed that PhMV has a 52% identity with *belladonna* mottle virus (E) and 33% identity with turnip yellow mosaic virus (TYMV), showing that PhMV (previously named as *belladonna* mottle virus 1) is a distinct Tymovirus. Thus, in certain embodiments, the Tymovirus virus and the Tymovirus VLP can be derived from PhMV.

PhMV is a small spherical plant virus of the Tymovirus genus of positive-stranded RNA viruses. The nucleotide sequence coding for the (PhMV) coat protein was identified from the GenBank having EMBL accession number S97776 (Jocob et al., 1992). The positive-sense RNA genome is encapsidated in a protein shell consisting of 180 identical copies of coat protein (CP) arranged with T=3 icosahedral symmetry. The multiple copies of the asymmetric unit provide regularly spaced attachment sites on both the internal and external surfaces of the PhMV capsid allowing for modification of PhMV with diagnostic and therapeutic agents described herein.

The coat protein of a *Tyrovirus* virus for use as a VLP can be synthetically produced using methods well known in the art. Methods of producing Tymovirus VLPs can include the steps of: (a) producing a recombinant polynucleotide sequence, (b) constructing a recombinant vector comprising a regulatory sequence and the recombinant polynucleotide sequence of step (a), (c) transforming a host cell with the recombinant vector of step (b) to produce a recombinant host cell, (d) growing the recombinant host cell of step (c) to produce Tymovirus virus-like particles, and (e) purifying the Tymovirus virus-like particles of step (d). The recombinant vector can further include a regulatory sequence. Exemplary regulatory sequence can include T7, SP6 and T3 promoters.

In an exemplary embodiment, Tymovirus-derived VLPs can be formed from Tymovirus structural proteins encoded by a recombinant poly nucleotide sequence that are expressed in an *Escherichia coli*, yeast or baculovirus heterologous expression system. In some embodiments, the heterologous expression system is an *E. coli* expression system. The *E. coli* strain can be selected from the group consisting of JM101, DH5α, BL21, HB101, BL21(DE3) pLys S, XL-1 Blue and Rossetta. In some embodiments, the recombinant poly nucleotide sequence can include, for example, a nucleotide sequence encoding all, or a truncated portion, of the PhMV coat protein.

Tymovirus Virus or Tymovirus VLP Functionalization

The invention makes use of a functionalized Tymovirus virus or Tymovirus VLP that have been loaded with or conjugated to one or more of a therapeutic agent, an imaging agent, or a targeting agent. Including a therapeutic agent, an imaging agent, or a targeting agent provides the capability for the virus particle to function as a targeted imaging agent or a targeted therapeutic agent. The ability of a Tymovirus virus or Tymovirus VLP to preferentially target cancer tissue can be further enhanced by loading or conjugating a targeting agent to the Tymovirus virus or Tymovirus VLP.

In some embodiments, therapeutic agents, imaging agents, and/or targeting agents (collectively referred to herein as agents) can be conjugated to the Tymovirus virus or Tymovirus VLP by any suitable technique, with appropriate consideration of the need for pharmacokinetic stability and reduced overall toxicity to the patient. The term "conjugating" when made in reference to an agent and a Tymovirus virus or Tymovirus VLP as used herein means covalently linking the agent to the virus. In certain embodiments, the nature and size of the agent and the site at which it is covalently linked to the virus particle do not interfere with the biodistribution of the modified virus and/or interfere with the internalization of the Tymovirus virus or Tymovirus VLPs by cancer cells.

Because viral capsids are proteinaceous, standard bioconjugation protocols that address chemically reactive amino acid side chains can be used as with other proteins. The most common reactions used to modify viruses involve the reactive side chains of lysine, cysteine and aspartic/glutamic acid residues, which are accessible to N-hydroxysuccinimidyl (NHS) chemistry, Michael addition to maleimides, and carbodiimide activation, respectively.

An agent can be conjugated to a Tymovirus virus or Tymovirus VLP either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). In addition, genetic modification can be applied to introduce any desired functional residue, including non-natural amino acids, e.g. alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the agent or the virus particle, and thus increase the coupling efficiency. A preferred group suitable for attaching agents to the Tymovirus virus particle or VLP are lysine residues present in the viral coat protein.

Suitable linkage chemistries include maleimidyl linkers and alkyl halide linkers and succinimidyl (e.g., N-hydroxysuccinimidyl (NHS)) linkers (which react with a primary amine on the plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, it can be desirable to use a linker group which is cleavable during or upon internalization into a cell, or which is gradually cleavable over time in the extracellular environment. A number of different cleavable linker groups have been described. The mechanisms for the intracellular release of a cytotoxic agent from these linker groups include cleavage by reduction of a disulfide bond (e.g., U.S. Pat. No. 4,489,710); by irradiation of a photolabile bond (e.g., U.S. Pat. No. 4,625,014); by hydrolysis of derivatized amino acid side chains (e.g., U.S. Pat. No. 4,638,045); by serum complement-mediated hydrolysis (e.g., U.S. Pat. No. 4,671,958); and acid-catalyzed hydrolysis (e.g., U.S. Pat. No. 4,569,789).

In some embodiments, more than one of a therapeutic agent, an imaging agent, or a targeting agent can be conjugated to a Tymovirus virus or Tymovirus VLP of the invention. By poly-derivatizing the Tymovirus virus or Tymovirus VLPs of the invention, several therapeutic (e.g., cytotoxic) strategies can be simultaneously implemented. For example, a plurality of Tymovirus virus or Tymovirus VLPs can be made useful as a contrasting agent for several visualization techniques, or a Tymovirus virus or Tymovirus VLP including a therapeutic agent can be labeled for tracking by a visualization technique. In one embodiment, multiple molecules of a therapeutic agent, an imaging agent, or a targeting agent are conjugated to a Tymovirus virus or Tymovirus VLP. In another embodiment, more than one type of a therapeutic agent, an imaging agent, or a targeting agent can be conjugated to a Tymovirus virus or Tymovirus VLP.

Non-Covalent Infusion of Imaging Agents and Cytotoxic Compounds

In some embodiments, Tymovirus virus or Tymovirus VLPs can be functionalized by loading with or conjugated to a therapeutic agent, an imaging agent, or a targeting agent through the use of non-covalent infusion techniques that facilitate efficient cargo loading of one or more of a therapeutic agent, an imaging agent, or a targeting agent into the virus or VLPs (See FIG. 1D, E). The three dimensional crystal structure of empty Tymovirus VLPs (e.g., PhMV-derived VLPs) correspond to a "swollen state" of the virus capable of cargo loaded via non-covalent infusion. To load cargo into Tymovirus virus or Tymovirus VLPs, Tymovirus virus or Tymovirus VLPs can be incubated in a bathing solution containing the guest molecule(s) (e.g., therapeutic agent, imaging agent, and/or targeting agent) at a molar excesses ranging from about 100 to about 10,000 molecules per VLP) in KP buffer with 10% (v/v) DMSO overnight at room temperature. After the reaction, excess guest molecules can be removed by ultracentrifugation and the amount of protein and cargo can be quantified by the Bradford assay and UV/visible spectroscopy, respectively.

It was found using TEM analysis that the Tymovirus VLP loaded with a cargo agent via non-covalent infusion maintain the approximately spherical structure of a wild-type particle and that there was no significant change in particles diameter (see FIG. 2D). It was further shown using fast protein liquid chromatography (FPLC) that the stability of the loaded VLPs can remain stable after months of storage in KP buffer at 4° C. with no evidence of particle aggregation.

Differences in loading efficiency may reflect the density and distribution of charged and hydrophobic groups on the guest molecules (e.g., a cytotoxic agent). For example, Tymovirus virus or Tymovirus VLPs typically have a greater affinity for cargo having a positive charge. Thus, in some embodiments, Tymovirus virus or Tymovirus VLPs are loaded with one or more positively charged therapeutic agents, imaging agents and/or targeting agents. In certain embodiments, cargo agent loaded PhMV is taken up by endocytosis and is trafficked to the lysosome where the protein carrier is degraded thus releasing the guest molecule (e.g., a cytotoxic agent) which diffuses into the cytosol and in the case of a cytotoxic agent, can kill the cells.

Imaging Agents

In some embodiments, the functionalized Tymovirus virus or Tymovirus VLPs are loaded with or conjugated to one or more imaging agents; i.e., the Tymovirus VLP comprises an imaging agent. Examples of imaging agents include fluorescent, radioactive isotopes, MRI contrast agents, enzymatic moieties, or detectable label of the invention. In some embodiments, the imaging agent is a fluorescent molecule for fluorescent imaging allowing, for example, quantification by UV/visible spectroscopy based on absorbance. In some embodiments, the imaging agent is a MRI contrast agent such as a chelated metal (e.g., Gd, Tb, or Dy).

The detectable group can be any material having a detectable physical or chemical property. Such detectable labels have been well-developed in the field of fluorescent imaging, magnetic resonance imaging, positive emission tomography, or immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), a triarylmethane dye (e.g., crystal violet), fluorescent dyes (e.g., fluorescein isothiocyanate, cyanines such as Cy5, Cy5.5 and analogs thereof (e.g., sulfo-Cyanine 5 NHS ester and Cy5.5 maleimide), Alexa Fluor dye (e.g., Alexa Fluor 647 and AlexaFluor 555), DyLight 649, Texas red, rhodamine B, and the like), radiolabels (e.g., $^3$H, $^{14}$C, $^{35}$S, $^{125}$I, $^{121}$I, $^{112}$In, $^{99}$mTc), other imaging agents such as microbubbles (for ultrasound imaging), $^8$F, $^{11}$C, $^{15}$O, (for Positron emission tomography), $^{99}$mTC, $^{111}$In (for Single photon emission tomography), gadolinium (Gd) chelate, terbium (Tb) chelate, dysprosium (Dy) chelate, europium (Eu) chelate, ytterbium (Yb) chelate or iron (for magnetic resonance imaging), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. See also Handbook of Fluorescent Probes and Research Chemicals, 6$^{th}$ Ed., Molecular Probes, Inc., Eugene Oreg., which is incorporated herein by reference. In some embodiments, the functionalized Tymovirus virus or Tymovirus VLPs are loaded with or conjugated to a contrast agent, such as gadolinium (Gd) chelate, and a fluorescent dye, such as Cy5.5.

The label may be conjugated directly or indirectly via a linker to the desired component of the Tymovirus virus or Tymovirus VLP according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include compounds of the Alexa Fluor® series (Invitrogen™), fluorescein and its derivatives, rhodamine and its derivatives (e.g., rhodamine B), dansyl, umbelliferone, and the like Chemiluminescent compounds include luciferin, and 2,3-dihydrophthalazinediones, e.g., luminol. For a review of various labeling or signal producing systems which may be used, see, U.S. Pat. No. 4,391,904, incorporated herein by reference.

In an exemplary embodiment, the surface exposed lysine residues of a Tymovirus virus or Tymovirus VLP are conjugated to NHS-activated esters of the fluorophore sulfo-cyanine 5 succinimidyl ester (sulfo-Cy5). Similarly the thiol grops on the internal cysteine residues of the Tymovirus virus or Tymovirus VLPs can be conjugated to Cy5.5-maleimide.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label.

In some embodiments, methods described herein can further include the step of imaging the cancer tissue in the subject using an imaging device wherein the cancer tissue is imaged subsequent to administering an effective amount of the plurality of Tymovirus virus or Tymovirus VLPs including one or more imaging agents. Examples of imaging methods include computed tomography, positive emission tomography, and magnetic resonance imaging.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues.

Therapeutic Agents

In certain embodiments, the Tymovirus virus or Tymovirus VLPs can be loaded with or conjugated to one or more therapeutic compounds, such as anti-cancer agents. In some embodiments, the Tymovirus virus or Tymovirus VLPs can be loaded with or conjugated to one or more anti-cancer agents, such as, but not limited to: acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decarbazine, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin 2 (including recombinant interleukin 2, or rIL2), interferon alpha-2a, interferon alpha-2b, interferon alpha-n1, interferon alpha-n3, interferon beta-I a, interferon gamma-I b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nitrosoureas, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride. Other anti-cancer drugs include, but are not limited to: 20-epi-1,25 dihydroxyvitamin D3,5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogens, antiestrogens, antineoplaston, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, dihydrotaxol, dioxamycin, diphenyl spiromustine, docetaxel, docosanol, dolasetron, doxifluridine, droloxifene, dronabinol, duocarmycin SA, ebselen, ecomustine, edelfosine, edrecolomab, eflomithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1 based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, R11 retinamide, rogletimide, rohitukine, romurtide, roquinimex, rubiginone B 1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, taxol, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thioguanine, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, and zinostatin stimalamer.

In some embodiments, the therapeutic compounds include cytotoxic compounds. It has been shown that the cytotoxicity of a therapeutic agent is not significantly affected by inclusion in a Tymovirus virus or Tymovirus VLP described herein. Thus, in certain embodiments, one or more cytotoxic compounds included in a Tymovirus virus or Tymovirus VLP retain their cytotoxic activity. The inclusion of a therapeutic agent in a Tymovirus virus or Tymovirus VLP that is preferentially internalized by cancer cells allows for the delivery of highly potent therapeutic agents to a subject's cancer cells while overcoming the dose-limiting toxicity of the drug towards healthy cells.

Cytotoxic compounds for use in a method or composition described herein include compounds that inhibit cell growth or promote cell death when proximate to or absorbed by a cell. Suitable cytotoxic compounds in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic compound can be, by way of non-limiting example, an antitumor agent, a photoactivated toxin or a radioactive agent.

Preferred radionuclides for use as cytotoxic compounds are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At can be conjugated to Tymovirus virus or Tymovirus VLPs for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodo-3-pyridinecarboxylate (SIPC). Any iodine isotope can be utilized in the recited iodo-reagents. Other radionuclides can be conjugated to the Tymovirus virus or Tymovirus VLPs by suitable chelation agents known to those of skill in the nuclear medicine arts.

In certain embodiments, cytotoxic compounds include small-molecule drugs such as doxorubicin, mitoxantrone, methotrexate, and pyrimidine and purine analogs, referred to herein as antitumor agents. Preferred chemotoxin differentiation inducers include phorbol esters and butyric acid. Antitumor agents can be directly conjugated to the Tymovirus virus or Tymovirus VLPs via a chemical linker, or can be encapsulated in a carrier, which is in turn coupled to the Tymovirus virus or Tymovirus VLPs. In certain embodiments, where encapsulation is not preferred or feasible, cytotoxic compounds or imaging agents can be directly infused into the Tymovirus virus or Tymovirus VLPs using a non covalent infusion protocol. For example, Tymovirus virus or Tymovirus VLPs can be incubated with a molar excess of about 500, about 2000, about 5000, or about 10000 cargo molecules (e.g., a dye or cytotoxic agent) per particle overnight at room temperature in the dark and then purified to remove excess reagents. In certain embodiments, the cytotoxicity of the free cytotoxic agent is not significantly affected by encapsulation by the Tymovirus virus or Tymovirus VLPs.

Preferred toxin proteins for use as cytotoxic compounds include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the patient, especially if injected intravascularly, it is preferred that they be encapsulated in a carrier for coupling to the Tymovirus virus or Tymovirus VLPs.

In certain embodiments of the invention, the Tymovirus virus or Tymovirus VLPs can be loaded with or conjugated to one or more photodynamic therapeutic photosensitizer (PDT sensitizer) compounds. Photodynamic therapeutic photosensitizer compounds are compounds that are excited by an appropriate light source to produce radicals and/or reactive oxygen species. Typically, when a sufficient amount of photosensitizer appears in diseased tissue (e.g., tumor tissue), the photosensitizer can be activated by exposure to light for a specified period. The light dose supplies sufficient energy to stimulate the photosensitizer, but not enough to damage neighboring healthy tissue. The radicals or reactive oxygen produced following photosensitizer excitation kill the target cells (e.g., cancer cells). In some embodiments, the targeted tissue can be locally illuminated. For example, light can be delivered to a photosensitizer via an argon or copper pumped dye laser coupled to an optical fiber, a double laser consisting of KTP (potassium titanyl phosphate)/YAG (yttrium aluminum garnet) medium, LED (light emitting diode), or a solid state laser.

PDT sensitizers for use in a method and/or composition described herein can include a first generation photosensitizer (e.g., hematoporphyrin derivatives (HpDs) such as Photofrin (porfimer sodium), Photogem, Photosan-3 and the like). In some embodiments, PDT sensitizers can include second and third generation photosensitizers such as porphyrinoid derivatives and precursors. Porphyrinoid derivatives and precursors can include porphyrins and mettaloporphrins (e.g., meta-tetra(hydroxyphenyl)porphyrin (m-THPP), 5,10,15,20-tetrakis(4-sulfanatophenyl)-21H, 23H-porphyrin (TPPS$_4$), and precursors to endogenous protoporphyrin IX (PpIX): 1,5-aminolevulinic acid (ALA), methyl aminolevulinate (MAL), hexaminolevulinate (HAL)), chlorins (e.g., benzoporphyrin derivative monoacid ring A (BPD-MA), meta-tetra(hydroxyphenyl)chlorin (m-THPC), N-aspartyl chlorin e6 (NPe6), and tin ethyl etiopurpurin (SnET2)), pheophorbides (e.g., 2-(1-hexyloxyethyl)-2-devinyl pyropheophorbide (HPPH)), bacteriopheophorbides (e.g., bacteriochlorphyll a, WST09 and WST11), Texaphyrins (e.g., motexafin lutetium (Lu-Tex)), and phtalocyanines (PCs) (e.g., aluminum phthalocyanine tetrasulfonate (AlPcS4) and silicon phthalocyanine (Pc4)). In some embodiments, the PDT sensitizer can include cationic zinc ethynylphenyl porphyrin.

Although porphyrinoid structures comprise a majority of photosensitizers, several non-porphyrin chromogens exhibit photodynamic activity. These compounds include anthraquinones, phenothiazines, xanthenes, cyanines, and curcuminoids.

Due in part to their preferential uptake/internalization by cancer cells over non-cancerous cells, functionalized Tymovirus virus or Tymovirus VLPs loaded with or conjugated one or more therapeutic agents (e.g., cytotoxic compounds or PDT agents) can be used to treat a variety of different types of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features.

A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In certain embodiments, the functionalized Tymovirus virus or Tymovirus VLPs are used to treat and/or image cancer tissue selected from the group consisting of ovarian, breast and prostate cancer.

Targeting Agents

In some embodiments, the Tymovirus virus or Tymovirus VLPs can additionally or optionally be loaded with or conjugated to one or more targeting agents that are capable of targeting and/or adhering the Tymovirus virus or Tymovirus VLPs to a cell or tissue of interest. In some embodiments, the use of targeting agents can enhance the delivery of the virus or VLPs to a targeted site and/or the preferential internalization of Tymovirus virus or Tymovirus VLPs exhibited by cancer cells over non-cancerous cells. The targeting agent can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting agent can interact with include molecules associated with a particular disease. For example, the biomarkers can include cell surface receptors implicated in cancer development, such as epidermal growth factor receptor and transferrin receptor, or cancer metastasis, such as $\alpha_v\beta_3$ or $\alpha_2\beta_1$ integrin. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting agents can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting agent can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting agent specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting agent need not originate from a biological source. The targeting agent may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting agent and select for a targeting agent with superior binding characteristics as compared to the un-mutated targeting agent. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting agents may be modified to make them more resistant to cleavage by proteases. For example, the stability of targeting agent comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting agent may be of the D configuration. The switch from L to D amino acids neutralizes the digestion capabilities of many of the ubiquitous peptidases found in the digestive tract. Alternatively, enhanced stability of a targeting agent comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting agent without affecting the activity or specificity of the interaction with a desired target molecule.

In certain embodiments, a targeting agent as described herein may comprise a homing peptide, which selectively directs the nanoparticle to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130:1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,6999; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the targeting agent may comprise a receptor molecule, including, for example, receptors, which naturally recognize a specific desired molecule of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chmokine receptor. Exemplary chemokine receptors have been described in, for example, Lapidot et al, 2002, Exp Hematol, 30:973-81 and Onuffer et al, 2002, Trends Pharmacol Sci, 23:459-67.

In some embodiments, the targeting agent can include cyclo (ARG-GLY-ASP-D-Phe-Cys) or (cRGDfC), which is a ligand for vascular targeting and metastasis. In some embodiments, a detergent compatible can be used to quantify the number of peptides per FeMSN particles.

In other embodiments, the targeting agent can be targeting peptide comprising an EGF peptide. The EGF peptide may comprise the amino acid sequence YHWYGYTPQNVI-amide. The peptide may be synthesized by any method known in the art. For example, the EGF peptide may be synthesized manually using Fmoc protected amino acids (Peptides International, Louisville, Ky.) on rink-amide CLEAR resin (Peptides International, Louisville, Ky., 100-200 mesh size, 0.4 milliequivalents/gram).

In still other embodiments, the targeting agent may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In other embodiments, the targeting agent may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting agent may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting agent to deliver the composition to a target cell. For instance, non-hydrolyzable peptide analogs of such resides can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

The targeting agent may be attached directly to the Tymovirus virus or Tymovirus VLP. In an exemplary embodiment, a targeting agent may be conjugated onto a Tymovirus virus or Tymovirus VLP via maleimide chemistry. In some embodiments, the targeting agent may be associated with or coupled to the nanoparticles using a linker. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

In some embodiments, the Tymovirus virus or Tymovirus VLPs can include multiple types of targeting moieties and the spacing and location of the targeting moieties on each nanoparticle can be controlled to facilitate delivery, targeting, and/or therapeutic efficacy of the nanoparticle cargo agent(s).

Immune Response to Virus-Like Particles

In some embodiments, administering a plurality of Tymovirus virus or Tymovirus VLPs to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the Tymovirus virus or Tymovirus VLPs is typically undesirable. Accordingly, in some embodiments it may be preferable to modify the Tymovirus virus or Tymovirus VLPs or take other steps to decrease the immune response. For example, an immunosuppressant compound can be administered to decrease the immune response. More preferably, the Tymovirus virus or Tymovirus VLPs can be modified to decrease its immunogenicity, such as through the use of shielding molecules that prevent immune clearance. Examples of methods suitable for decreasing immunity include attachment of anti-fouling (e.g., zwitterionic) polymers, glycosylation of the virus carrier, and PEGylation.

In some embodiments, the immunogenicity of the Tymovirus virus or Tymovirus VLPs are decreased by PEGylation. PEGylation is the process of covalent attachment of polyethylene glycol (PEG) polymer chains to a molecule, such as a Tymovirus VLP. PEGylation can be achieved by incubation of a reactive derivative of PEG with the Tymovirus virus or Tymovirus VLP. The covalent attachment of PEG to the Tymovirus virus or Tymovirus VLP can "mask" the agent from the host's immune system, and reduce production of antibodies against the carrier. PEGylation also may provide other benefits. PEGylation can be used to vary the circulation time of the Tymovirus virus or Tymovirus VLPs. For example, use of PEG 5,000 can provide a virus-like particle with a circulation half-life much lower than the use of PEG 20,000.

The first step of PEGylation is providing suitable functionalization of the PEG polymer at one or both terminal positions of the polymer. The chemically active or activated derivatives of the PEG polymer are prepared to attach the PEG to the Tymovirus virus or Tymovirus VLPs. There are generally two methods that can be used to carry out PEGylation; a solution phase batch process and an on-column fed-batch process. The simple and commonly adopted batch process involves the mixing of reagents together in a suitable buffer solution, preferably at a temperature between 4° and 6° C., followed by the separation and purification of the desired product using a chromatographic technique.

Administration and Formulation of Tymovirus Virus or Tymovirus VLPs

In some embodiments, a plurality of Tymovirus virus or Tymovirus VLPs are administered together with a pharmaceutically acceptable carrier to provide a pharmaceutical formulation. Pharmaceutically acceptable carriers enable the Tymovirus virus or Tymovirus VLPs to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the Tymovirus virus or Tymovirus VLPs into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated functionalized Tymovirus virus or Tymovirus VLPs can be administered as a single dose or in multiple doses.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the Tymovirus virus or Tymovirus VLPs vary depending upon many different factors, including means of administration, target site, physiological state of the patient, whether the patient is human or an animal, other medications administered, and whether treatment is prophylactic or therapeutic.

The dosage of an imaging agent, therapeutic agent, and/or targeting agent including in a plurality of Tymovirus virus or Tymovirus VLPs for administration to a mammalian subject or an avian subject in accordance with a method described herein ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of Tymovirus virus or Tymovirus VLPs are used to provide the desired dosage of agent(s). An exemplary treatment regime entails administration once per every two weeks or once a month or once every 3 to 6 months. The plurality of Tymovirus virus or Tymovirus VLPs are usually administered on multiple occasions. Alternatively, the Tymovirus virus or Tymovirus VLPs can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patient subject can be administered a prophylactic regime.

Compositions including Tymovirus virus or Tymovirus VLPs described herein can also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized SEPHAROSE, agarose, cellulose, and the like), polymeric amino acids, amino acid copolymers, and lipid aggregates (such as oil droplets or liposomes).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

In other embodiments, Tymovirus virus or Tymovirus VLPs can be administered to a subject in a method of detecting cancer. The method includes administering a plurality of functionalized Tymovirus virus or Tymovirus VLPs that have been loaded with or conjugated to an imaging agent. The method also includes detecting the imaging agent in the subject using an imaging device subsequent to administering the Tymovirus virus or Tymovirus VLPs to determine the location and/or distribution of the cancer in the subject. The cancer can be detected in a particular area or portion of the subject and, in some instances, two or more areas or portions throughout the entire subject. For example, the cancer can be detected in diseased tissue, including neoplastic or cancerous tissue (e.g., tumor tissue). The cancer can include a solid tumor, such as a solid carcinoma, sarcoma or lymphoma. The tumor can include both cancerous and pre-cancerous cells. The detected cancer can include malignant cancer metastases.

The particular area or portion of the subject can include regions to be imaged for both diagnostic and therapeutic purposes. The particular cancerous area or portion of the subject where cancer is detected is typically internal; however, it will be appreciated that the cancer may additionally or alternatively be external.

At least one image of the particular cancerous area or portion of the subject can be generated using an imaging agent once the Tymovirus virus or Tymovirus VLPs localize to the cancer. The imaging agent can include one or combination of known imaging techniques capable of visualizing the virus or VLPs. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET).

In one example, the imaging agents loaded with or conjugated to the virus or VLPs can be detected with MRI and/or x-ray. MRI relies upon changes in magnetic dipoles to perform detailed anatomic imaging and functional studies.

Optionally, the Tymovirus virus or Tymovirus VLPs can be modified to facilitate detection and imaging with MRI and CT as well as positron emission tomography (PET). For MRI applications, gadolinium tags can be attached to the conjugated to or loaded in the VLPs. For PET applications, radioactive tags can be attached to virus or VLPs. For CT applications, iodide or other heavy metals can be attached to the Tymovirus virus or Tymovirus VLPs to facilitate CT contrast.

It will be appreciated that the Tymovirus virus or Tymovirus VLPs will likely be most useful clinically when several imaging techniques or imaging followed by a medical or surgical procedure is used. In this way, the ability to use one agent for multiple imaging modalities is optimized making the Tymovirus virus or Tymovirus VLPs cost-competitive with existing contrast agents.

For multimodal imaging applications, the Tymovirus virus or Tymovirus VLPs can be administered to a subject and then preoperatively imaged using, for example, CT or MRI. After preoperative imaging, the Tymovirus virus or Tymovirus VLPs can serve as optical beacons for use during surgery leading to more complete resections or more accurate biopsies. In surgical resection of lesions, the completeness of resection can be assessed with intra-operative ultrasound, CT, or MRI. For example, in prostate cancer or breast cancer surgery, the Tymovirus virus or Tymovirus VLPs can be given intravenously about 24 hours prior to pre-surgical stereotactic localization MRI. The viral nanoparticles can be imaged on gradient echo MRI sequences as a contrast agent that localizes with a prostate or breast cancer tumor.

The present invention is illustrated by the following examples. It is to be understood that the particular examples, materials, amounts, and procedures are to be interpreted broadly in accordance with the scope and spirit of the invention as set forth herein.

EXAMPLE

Physalis Mottle Virus-Like Particles as Nanocarriers for Imaging Reagents and Drugs In this example, we describe VLPs based on Physalis mottle virus (PhMV) and their use for imaging and drug delivery. PhMV (Tymovirus, Tymoviridae) has an about 30-nm icosahedral capsid with T=3 symmetry, containing a single-stranded, plus-sense RNA genome of 6.67 kb. The genome is encapsidated in a protein shell comprising 180 chemically identical 21 kDa coat protein subunits, with three distinct bonding patterns (A, B and C). The A type subunits form pentamers at the icosahedral five-fold axes (60 subunits), whereas the B and C type subunits form 20 hexamers at the icosahedral three-fold axes (120 subunits). The protein subunits are held in place by strong protein-protein interactions. The multiple copies of the asymmetric unit provide regularly spaced attachment sites on both the internal and external surfaces of the PhMV capsid. The PhMV coat protein expressed in E. coli was shown to self-assemble into stable VLPs that were nearly identical to the viruses formed in vivo. These VLPs can be purified in large quantities (50-100 mg/L) and are exceptionally robust, maintaining their integrity within the pH range 4.2-9.0 and in the presence of up to 5 M urea. They are monodisperse, symmetrical and polyvalent. Neither the deletion nor the addition of amino acids at the N-terminus of the PhMV coat protein hinders capsid assembly, making this an ideal site for modifications. The three-dimensional crystal structures of PhMV and its empty capsid have been determined to 3.8 and 3.2 Å resolution, respectively. The structures indicate that the empty shells correspond to a "swollen state" of the virus, with increased disorder in the N-terminal segments as well as some positively charged side chains lining the internal cavity.

PhMV-derived VLPs have been genetically engineered to display diagnostic and immunogenic epitopes. PhMV offers the following advantages:

(1) The genome is small (2) It is easy to manipulate (3) Purification is simple and quicker than the regeneration of stably transformed plants. Coat protein of PhMV expresses extremely well as empty capsids in E. coli resulting in (1) Yields as high as 100-150 irmg per liter of culture, (2) Batch to batch variations are nil as each and every time confirmation of the assembled capsids will be maintained in a similar way for the integrity of the capsids, (3) Recombinant Ph-CP is stable over a wide range of pH from 4.2 to 9.0 and stable upto 4 M urea, (4) Purification of empty capsids is easy (5) Mechanism of assembly of empty capsids is well studied. (6) Host range is very narrow.

Here, we show the internal and external surface chemistries of PhMV and developed protocols to achieve the specific functionalization of these surfaces with different reagents. A library of functionalization protocols, including bioconjugation and non-covalent infusion, was used to modify PhMV with dyes, drugs and photosensitizers. These functionalized PhMV nanoparticles were then characterized by flow cytometry and confocal microscopy, and their cytotoxic efficacy was tested in a range of normal and cancer-derived cell lines.

Methods

Expression and Purification of PhMV VLPs

The 564-bp PhMV coat protein gene (GenBank S97776) was prepared as a synthetic construct by Invitrogen GeneArt, with XhoI and HindIII sites at the 5' and 3' ends, respectively, for insertion into pRSET-A (Invitrogen) at the same sites. The integrity of the recombinant vector (pR- PhMV-CP) was confirmed by automated DNA sequencing before the transformation of ClearColi BL21(DE3) cells. The expression and purification of PhMV VLPs is described. Briefly, a single colony carrying pR-PhMV-CP was inoculated into 50 mL of lysogeny broth (LB) containing 100 mg/mL ampicillin and was incubated for 20 h at 37° C. We then used 5 mL of the pre-culture to inoculate 500 mL LB with ampicillin as above. After 4-5 h of growth ($OD_{600\ nm}$=0.6), expression was induced with 0.5 mM IPTG and the cells were incubated at 30° C. overnight. The culture was centrifuged (6000 rpm, 10 min, 4° C.) and the pellet was suspended in 50 mM sodium citrate buffer, pH 5.5 (SCB). The suspension was then sonicated and centrifuged at 35,000 rpm using a 50.2 Ti rotor (Beckman Coulter Inc.) at 4° C. for 3 h. The pellet was resuspended in SCB and layered onto a 10-40% linear sucrose gradient and centrifuged at 28,000 rpm in an SW 32 Ti rotor (Beckman Coulter Inc.) at 4° C. for 3 h. The light scattering zone was collected with a Pasteur pipette, diluted with SCB and centrifuged at 42,000 rpm using 50.2 Ti rotor at 4° C. for 3 h. The final pellet was resuspended in SCB and stored at 4° C. The protein concentration was measured using Bradford reagent (BioRad).

Bioconjugation Reactions

External lysine residues were conjugated to sulfo-Cy5 NHS ester (Lumiprobe), whereas internal cysteine residues were conjugated to Cy5.5-maleimide (Lumiprobe). The dyes were added to PhMV at a concentration of 1 mg/mL in KP buffer (0.01 M potassium phosphate buffer pH 7.0) at a molar excess of 900 Cy5 molecules per particle (five molecules per coat protein) and 360 Cy5.5 per particle (two molecules per coat protein). The final DMSO concentration was adjusted to 10% (v/v). The reaction was left for 2 h (Cy5) or overnight (Cy5.5) at room temperature with agitation in the dark. Both reaction mixtures were purified over a 30% (w/v) sucrose cushion by ultracentrifugation at 52,000 rpm using a TLA55 rotor (Beckman Coulter Inc.) for 1 h. Pellets containing dye-labeled particles were resuspended in KP buffer overnight at 4° C. For PhMV-$K_E$-Cy5 particles, 10 kDa molecular weight cutoff (MWCO) centrifugal filters (Amicon) were also used to remove excess dye molecules. Any aggregates were removed by a clearing spin at 12000 rpm for 10 min using a table-top centrifuge. For the biotin conjugation reactions, the VLPs were used at a final concentration of 1 mg/mL in KP buffer and were incubated with a 360-fold molar excess of biotin (biotin-NHS ester or biotin-maleimide) at room temperature overnight, with agitation. The final DMSO concentration was adjusted to 10% of the reaction volume. Particles were purified using 10 kDa MWCO centrifugal filter units (Millipore).

Infusion Protocol

The VLPs were loaded with rhodamine B, fluorescein, crystal violet, MTX dihydrochloride (all Sigma-Aldrich), PS (cationic zinc ethynylphenyl porphyrin, full name 5-(4-ethynylphenyl)-10,15,20-tris)4-methylpyridin-4-ium-1-yl) porphyrin zinc(II) triiodide), or DOX hydrochloride (Indofine Chemical Company). The VLPs (1 mg/mL in KP buffer) were incubated with a molar excess of 500, 2500, 5000, or 10000 cargo molecules per particle overnight at room temperature in the dark, before purification over a 30% (w/v) sucrose cushion to remove excess reagents by ultracentrifugation at 52,000 rpm using a TLA 55 rotor (Beckman Coulter Inc.) at 4° C. for 1 h. PS-PhMV and DOX-PhMV were synthesized for further characterization using a 5000-fold molar excess.

UV/Visible Spectroscopy

A NanoDrop 2000 spectrophotometer (Thermo Fisher Scientific) was used to characterize the UV/visible spectra of native and modified VLPs. The dye load was determined using the protein concentration (measured using the Bradford assay), the Beer-Lambert law and the following dye-specific extinction coefficients: rhodamine B, $\varepsilon$(553 nm)=116,000 $M^{-1}$ $cm^{-1}$; DOX, $\varepsilon$(496 nm)=11,500 $M^{-1}$ $cm^{-1}$; crystal violet, $\varepsilon$(590 nm)=87,000 $M^{-1}$ $cm^{-1}$; PS, $\varepsilon$(450 nm)=195,000 $M^{-1}$ $cm^{1}$; MTX, $\varepsilon$(622 nm)=25,000 $M^{-1}$ $cm^1$; sulfo-Cy5 NHS ester, $\varepsilon$(646 nm)=271,000 $M^{-1}$ $cm^{-1}$; Cy5.5-maleimide, 8(673 nm)=209,000 $M^{-1}$ $cm^{-1}$. The following molecular weights were used: PhMV=4.7×10$^6$ g $mol^{-1}$; rhodamine B=479.02 g $mol^{-1}$; DOX=579.98 g $mol^{-1}$; crystal violet=407.98 g $mol^1$; PS=1130 g $mol^{-1}$; mitoxantrone=517.4 g $mol^{-1}$; Cy5=777.95 g $mol^{-1}$; Cy5.5=741.36 g $mol^{-1}$; Biotin NHS ester=341.38 g $mol^{-1}$; Biotin maleimide=451.54 g $mol^{-1}$.

Native and Denaturing Gel Electrophoresis

Intact VLPs (10-20 µg per lane) were analyzed by 1% (w/v) agarose native gel electrophoresis in 0.1 M Tris-maleate running buffer (pH 6.5) as previously described. Denatured protein subunits (10 µg per lane) were analyzed by polyacrylamide gel electrophoresis using 4-12% NuPAGE gels and 1×MOPS buffer (Invitrogen). Samples were denatured by boiling in SDS loading dye for 10 min. Gels were photographed under UV or white light before staining with Coomassie Blue, and under white light after staining, using an AlphaImager system (Biosciences).

Size Exclusion Chromatography

VLPs were analyzed by SEC using a Superose-6 column on the AkTA Explorer system (GE Healthcare). The column was loaded with 100 µL samples (1 mg/mL) at a flow rate of 0.5 mL $min^{-1}$ in KP buffer.

Transmission Electron Microscopy

VLPs suspended at 1 mg/mL in 20 µL KP buffer were deposited onto Formvar carbon film coated copper TEM grids (Electron Microscopy Sciences) for 2 min at room temperature. The grids were then washed twice with deionized water for 45 s and stained twice with 2% (w/v) uranyl acetate in deionized water for another 30 s. A Tecnai F30 transmission electron microscope was used to analyze the samples at 300 kV.

Zeta Potential Analysis

The zeta potential ($\zeta$) of the VLPs was determined by placing 0.25 mg/mL solutions of each VLP in a 90Plus Zeta potential analyzer (Brookhaven Instruments) and conducting five measurements, each comprising six runs.

Avidin Agarose Affinity Binding Assay

Biotinylated VLPs and controls were tested for their ability to bind avidin agarose resin (Pierce). The batch method provided by the supplier was used, with some modifications: 100 µg samples in 100 µL binding buffer (PBS with 0.1% SDS and 1% NP-40) were added to 100 µL of the resin, and the resulting 200 µL of slurry was mixed for 1 h at room temperature. The supernatant was then recovered and the resin washed six times in 100 µL binding buffer. Bound VLPs were eluted in 100 µL 0.1 M glycine-HCl buffer (pH 2.8) and the pH was immediately adjusted with 10 µL 1 M Tris buffer (pH 7.5). Samples of the wash fractions and the eluate were analyzed by denaturing gel electrophoresis, 30 µL per lane.

Tissue Culture

All cell lines were obtained from the American Type Culture Collection (ATCC). HeLa (cervical cancer), RAW264.7 (leukemic macrophages), A2780 (ovarian cancer), MDA-MB-231 (breast cancer) and U87 (brain cancer) cell lines were maintained in Dulbecco's modified Eagle's medium (DMEM) supplemented with 10% (v/v) fetal bovine serum (FBS, Atlanta Biologicals), 1% (w/v) penicillin/streptomycin (pen/strep, Thermo Fisher Scientific) and 1% (w/v) glutamine, at 37° C. and 5% $CO_2$. HT1080 (fibrosarcoma) cells were maintained in Minimum Essential Medium (MEM) supplemented with 10% (v/v) FBS, 1% (w/v) pen/strep and 1% (w/v) glutamine as above. PC-3 cells (prostate cancer) were maintained in Roswell Park Memorial Institute (RPMI) 1640 medium supplemented with 10% (v/v) FBS, 1% (w/v) pen/strep and 1% (w/v) glutamine as above. NIH3T3 murine fibroblasts were maintained in DMEM/F12 medium containing 10% (v/v) newborn calf serum, 1% (w/v) pen/strep and 1% (w/v) GlutaMax as above.

Confocal Microscopy

Cell lines were grown for 24 h on glass coverslips (25,000 cells per well) placed in an untreated 24-well plate in 200 µL of the appropriate medium. The cells were washed twice with Dulbecco's PBS (DPBS) before adding the PhMV-$K_E$-Cy5 or PhMV-$C_I$-Cy5.5 particles ($2.5 \times 10^6$ particles per cell, corresponding to ~0.5 µg/well) and incubating for 6 h. The cells were washed twice in DPBS to remove unbound particles and fixed for 5 min at room temperature in DPBS containing 4% (v/v) paraformaldehyde and 0.3% (v/v) glutaraldehyde. Cell membranes were stained with 1 µg/mL wheat germ agglutinin conjugated to AlexaFluor-555 (Invitrogen) diluted 1:1000 in DPBS containing 5% (v/v) goat serum, and the cells were then incubated for 45 min at room temperature in the dark. Finally, the cells were washed thrice with DPBS, and the coverslips were mounted on glass slides using Fluroshield with 4', 6-diamidino-2-phenylindole (DAPI, Sigma-Aldrich) and sealed using nail polish. Confocal images were captured on a Leica TCS SPE confocal microscope and the images were processed using Image J v1.44o.

For co-localization studies, A2780 and MDA-MB-231 cells were incubated for 6 h with PhMV-$C_I$-Cy5.5 particles, then blocked in 10% (v/v) goat serum for 45 min to reduce non-specific antibody binding. Endolysosomes were stained using a mouse anti-human LAMP-1 antibody (Biolegend) diluted 1:250 in 5% goat serum for 60 min, with DAPI staining and imaging as described above. VLPs were visualized by detecting the covalently-attached Cy5.5 maleimide dye as described above.

Fluorescence-Activated Cell Sorting

Cells were grown to confluency, collected in enzyme-free Hank's-based cell dissociation buffer, and distributed in 200 µL aliquots at a concentration of $2 \times 10^5$ cell/mL in V-bottom 96-well plates. Dye-labeled VLPs (100,000 particles per cell, corresponding to ~1.6 µg/well) were added to the cells and incubated for 6 h. The cells were washed twice in FACS buffer (0.1 mL 0.5 M EDTA, 0.5 mL FBS, and 1.25 mL 1 M HEPES, pH 7.0 in 50 mL $Ca^{2+}$ and $Mg^{2+}$ free PBS) and fixed in 2% (v/v) formaldehyde in FACS buffer for 10 min at room temperature. Cells were washed and resuspended in FACS buffer and analyzed using a BD LSR II flow cytometer. Triplicates of each sample were maintained and at least 10,000 events (gated for live cells) were recorded. Data were analyzed using FlowJo v8.6.3.

LIVE/DEAD Assay

PC-3 cells were seeded (20,000 cells/500 L RPMI/well) in a 24-well plate overnight. The cells were washed twice in PBS and incubated for 8 h in triplicates with 5.0 µM PS, 5.0 µM PS-PhMV, or the corresponding concentration of unloaded VLPs (236.70 M or ~0.19 mg/mL). After washing twice in PBS, 500 µL RPMI medium was added. Photodynamic therapy was then applied using a white light source (Phillips Silhouette High Output F39T5/841 HO, Alto collection, ~10 mW $cm^{-2}$) for 30 min (18.1 J $cm^{-2}$ at 430 nm) and cells were incubated for a further 48 h in the dark. Cell viability was determined using a LIVE/DEAD assay for mammalian cells (Thermo Fisher Scientific) following the manufacturer's procedures for cell staining, and cells were observed under a Zeiss Axio Observer Z1 motorized FL inverted microscope.

MTT Cell Viability Assay

PC-3 cells were seeded (5000 cells/100 µL RPMI 1640/well) in a 96-well plate overnight. After two PBS washes to remove unbound and dead cells, free PS, or PS-PhMV was added to the cells in triplicate at concentrations of 0.01, 0.025, 0.05, 0.1, 0.25, 0.5, 1, 2.5 and 5.0 µM PS, and incubated for 8 h. Untreated cells and cells treated with unloaded VLPs at the equivalent protein concentration to PS-PhMV particles at the highest dose of PS were also used as controls. Free particles were washed with PBS and 100 µL of fresh medium was added. The cells were then illuminated with white light for 30 min as above. In parallel, a duplicate plate was prepared and kept in the dark as a negative control. Following phototherapy, cells were incubated for another 48 h in the dark, and their viability was subsequently measured using an MTT cell proliferation assay kit (ATCC) based on the manufacturer's instructions. A Tecan Infinite 200 PRO multimode plate reader was used to measure absorbance at 570 nm, and the percent cell viability was normalized to the untreated control. All assays were carried out at least three times. The efficacy of DOX-PhMV was tested by seeding A2780 and MDA-MB-231 cells as above (5000 cells/100 µL DMEM/well) and treating triplicate wells with free DOX or DOX-PhMV at concentrations of 0.01, 0.05, 0.1, 0.5, 1, 5.0 and 10.0 µM DOX for 24 h. Untreated cells and cells treated with unloaded VLPs at a concentration equivalent to the highest dose of DOX-PhMV were used as controls. Washing steps and the MTT assay were then carried out as above.

Results

Purification and Characterization of PhMV-Derived VLPs Produced in ClearColi Cells PhMV-derived VLPs were purified from ClearColi cells to avoid endotoxin contamination. The coat protein gene (564 bp) was inserted into the vector pRSET-A and expressed in ClearColi BL21(DE3). Optimum expression was achieved by inducing the culture with 0.5 mM isopropyl β-D-1-thiogalactopyranoside (IPTG) and cultivating at 30° C. overnight. SDS-PAGE analysis confirmed the presence of the coat protein in total and soluble cell protein extracts and VLPs were purified from the soluble fraction. A single light-scattering zone was observed in a 10-40% (w/v) linear sucrose density gradient and the VLP yield was 40-50 mg per liter of culture medium, as determined using the Bradford assay.

The denatured VLP preparation revealed a single 26 kDa band corresponding to the coat protein. Fast protein liquid chromatography (FPLC) analysis confirmed that the particles eluted as a single peak at 7.5 mL, indicating they were intact and stable (Figure S1D). Transmission electron microscopy (TEM) revealed that the VLPs were approximately spherical and 29±2 nm in diameter, indicating that recombinant PhMV coat proteins were indeed capable of self-assembly. The zeta potential of the VLPs was +4.20±0.46 (Table 1).

TABLE 1

Zeta potential measurement of functionalized PhMV

| Sample | Zeta potential (Standard error in parenthesis) |
|---|---|
| Native PhMV | +4.20 (0.46) |
| PhMV-$K_E$ Cy5 | −7.92 (2.49) |
| PhMV-$C_I$ Cy5.5 | +0.38 (3.32) |
| DOX-PhMV | +9.38 (1.93) |
| PS-PhMV | −0.81 (3.08) |

Structure-Based Design of PhMV-Derived VLPs to Carry Dyes and Drugs

A reliable PhMV-based platform for chemical modification requires the identification of attachment sites on the capsid that do not compromise the structure of the asymmetric unit and its native biological functions, but nevertheless allow for efficient bioconjugation reactions. The bioconjugation sites on the internal and external surfaces of the VLP were chosen by studying the structural contribution of each residue. Nine lysine residues are present on each PhMV coat protein subunit, four of which (K62, K143, K153, and K166) are exposed on the exterior, resulting in 720 addressable lysine residues per VLP that can be used for bioconjugation based on lysine/N-hydroxysuccinimide (NHS) ester chemistry (FIG. 1A). The coat protein contains only a single cysteine residue (C75) and this is presented on the internal surface, resulting in 180 addressable cysteine residues per VLP potentially suitable for bioconjugation using thiol-maleimide chemistry (FIG. 1A). As well as the development of bioconjugation protocols (FIGS. 1B, C), we also considered the encapsulation of cargo molecules in the cavity. The encapsulation of dyes and drugs via particle disassembly and assembly is not possible in the case of PhMV because the virus is stabilized predominantly by protein-protein interactions. We therefore developed an infusion protocol to load the VLPs with cargo (FIGS. 1D-E).

Bioconjugation of PhMV-Derived VLPs with Dyes

Surface-exposed lysine residues were conjugated to NHS-activated esters of sulfo-cyanine 5 succinimidyl ester (sulfo-Cy5) by incubating for 2 h with a 900-fold molar excess of the dye, equivalent to five dye molecules per coat protein (FIG. 1B). Similarly, the thiol groups on the internal cysteine residues were conjugated overnight using Cy5.5-maleimide at a 360-fold molar excess, equivalent to two dye molecules per coat protein (FIG. 1C). The resulting VLP-dye conjugates (PhMV-$K_E$-Cy5 and PhMV-$C_I$-Cy5.5, where $K_E$=external lysine and $C_I$=internal cysteine) were purified by ultracentrifugation, and PhMV-$K_E$-Cy5 was purified further by ultrafiltration to remove free dye molecules. The Bradford protein assay was used to estimate the concentration of PhMV-$K_E$-Cy5 and PhMV-$C_I$-Cy5.5 particles. UV/visible spectroscopy was used to determine the number of dye molecules per particle based on the Beer-Lambert law and dye-specific extinction coefficients, revealing that the PhMV-$K_E$-Cy5 particles contained 160-180 Cy5 molecules and the PhMV-$C_I$-Cy5.5 particles contained 40-60 Cy5.5 molecules. The higher labeling efficiency achieved using lysine-NHS chemistry was expected due to the presence of 720 surface-exposed lysine residues compared to 180 internal cysteine residues.

Increasing the molar excess of Cy5.5-maleimide did not increase the internal labeling density, and maximum labeling efficiency was achieved with two dye molecules per coat protein. In contrast, we achieved a greater density of external labeling when the molar excess of sulfo-Cy5 was increased to 20 dye molecules per coat protein but further increases were not tested because the dye aggregated at higher concentrations. For imaging applications, the spatial distribution of dye molecules is important, so we measured the distance between the surface-exposed lysine side chains using Chimera software and found the spacing lies between 1-5 nm. However, if we assume random distribution of the Cy5 molecules conjugated to the external lysine side chains, the average distance between two fluorophores would be ~2-4 nm assuming 1-2 dyes per coat protein. Based on the Foerster radius, which suggests quenching generally occurs when dyes are <10 nm apart, we would expect quenching to occur for the labeled VLPs due to cross-talk between the fluorophore centers. Nevertheless, detection was not an issue for these particles. Furthermore, when taken up by cells, the dyes are on these particles are likely to be cleaved from the VLP as has been previously shown. Further structure-function studies would be required for the development of fluorophore-labeled PhMV VLPs as optical probes.

We characterized the PhMV-$K_E$-Cy5 and PhMV-$C_I$-Cy5.5 particles using a combination of native and denaturing gel electrophoresis, zeta potential analysis, FPLC, and TEM. Native and denaturing gel electrophoresis followed by visualization under white light before Coomassie staining confirmed the covalent attachment of the dyes (FIGS. 2A, B; lanes 2, 3). The charge of the PhMV-$K_E$-Cy5 particles was altered following bioconjugation, as evident from the mobility shift towards the anode during native electrophoresis (FIG. 2B, lane 2). This was anticipated because the addition of the non-charged dye removes positive amines from the particle surface and thus reduces the overall positive surface charge. Accordingly, zeta potential measurements revealed that the PhMV-$K_E$-Cy5 particles were negatively charged (−7.92) whereas native PhMV particles are positively charged (+4.20) (Table 1). In contrast, the mobility of the PhMV-$C_I$-Cy5.5 particles was the same as wild-type PhMV because cysteine residues are uncharged (FIG. 2B, lane 3). Zeta potential measurements indicated a reduction in the net positive charge of the PhMV-$C_I$-Cy5.5 particles (+0.38), probably reflecting changes in surface charge distribution.

FPLC and TEM analysis indicated that the dye-labeled VLPs were intact. Dye-labeled particles eluted as a single peak from the Superose-6 column at an elution volume of 7.5 mL, the same as wild-type particles, and the fluorophore co-eluted with the PhMV-$K_E$-Cy5 and PhMV-$C_I$-Cy5.5 particles at 646 nm and 673 nm, respectively (FIG. 2C; top panel). TEM analysis revealed that the labeled particles remained monodisperse, with a diameter of 28-29 nm based on ImageJ analysis (FIG. 2D; top panel). Finally, the labeled particles remained stable when stored at 4° C. in KP buffer (0.01 M potassium phosphate, pH 7.0) for several months.

Spatial Distribution of Biotin in VLP-Biotin Conjugates

Figure 3D:
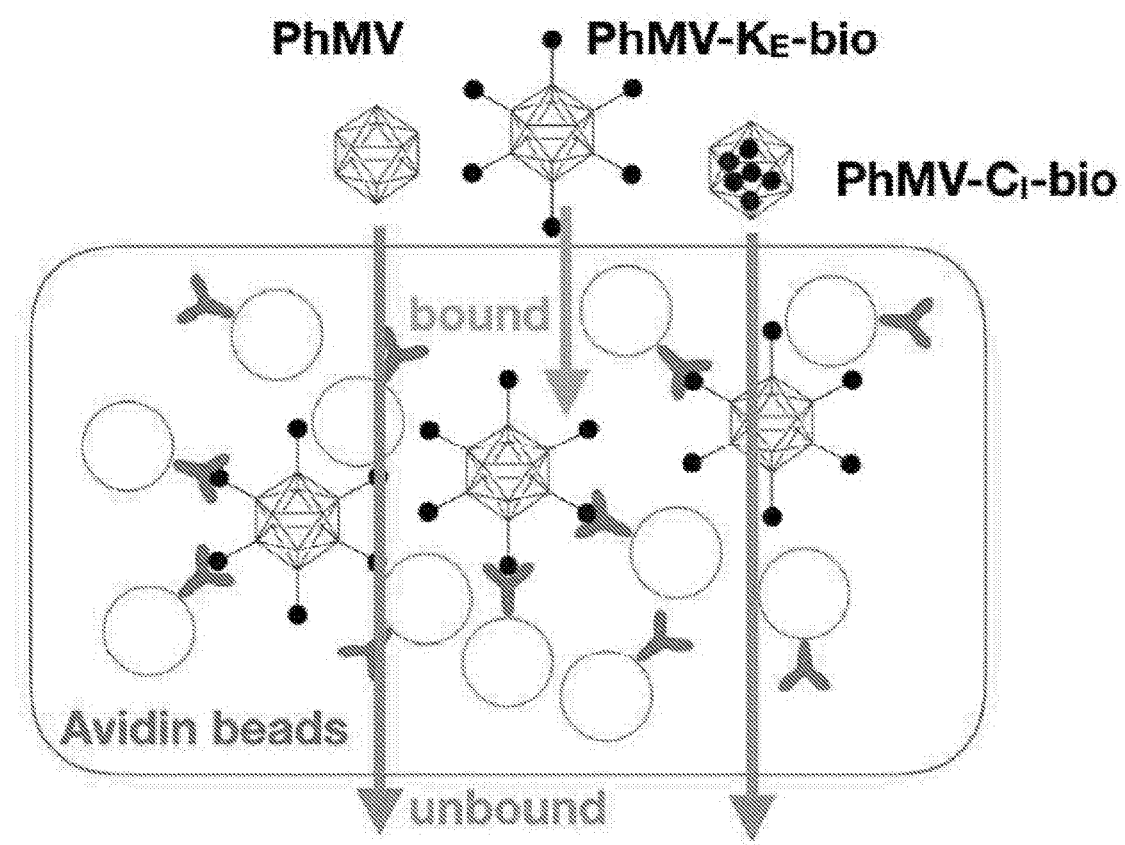
FIGS. 3(A-D) illustrate the characterization of PhMV-biotin conjugates. (A) Biotinylated PhMV particles separated by denaturing SDS-PAGE visualized after staining with Coomassie. M=SeeBlue Plus2 molecular weight marker. 1. Native PhMV; 2. PhMV-CI-bio; 3. PhMV-KE-bio. (B) Biotinylated PhMV particles separated by agarose gel electrophoresis visualized after Coomassie staining. (C) Flow through and eluted biotinylated particles from avidin bead binding assay separated by SDS-PAGE and stained with Coomassie. 4. Native PhMV flow through; 5. PhMV-KE-bio flow through; 6. PhMV-CI-bio flow through; 7. Bound native PhMV; 8. Bound PhMV-KE-bio; 9. Bound PhMV-CI-bio. (D) Avidin bead assay: PhMV samples are exposed to avidin-coated beads; only particles with biotin on the external surface bind to the beads.

To confirm the position of the bioconjugation sites, we modified each site with biotin labels and mapped them using an avidin bead assay. This was necessary because although maleimide chemistry is thiol selective, some reports indicate cross-reactivity with lysine residues. External lysine residues were therefore labeled using a 360-fold molar excess of a NHS-reactive biotin probe to generate PhMV-$K_E$-bio particles, and internal cysteine residues were labeled using a 360-fold molar excess of a maleimide-reactive biotin probe to generate PhMV-$C_I$-bio particles. The resulting particles were analyzed by native and denaturing gel electrophoresis. As expected, we observed no difference in mobility between labeled and unlabeled particles in the denaturing gels (FIG. 3A), whereas the mobility of PhMV-$K_E$-bio but not PhMV-$C_I$-bio differed from the unlabeled particles in the native gels due to the elimination of positive surface charges, consistent with the behavior of the dye-labeled particles above (FIG. 3B).

Figure 4C:
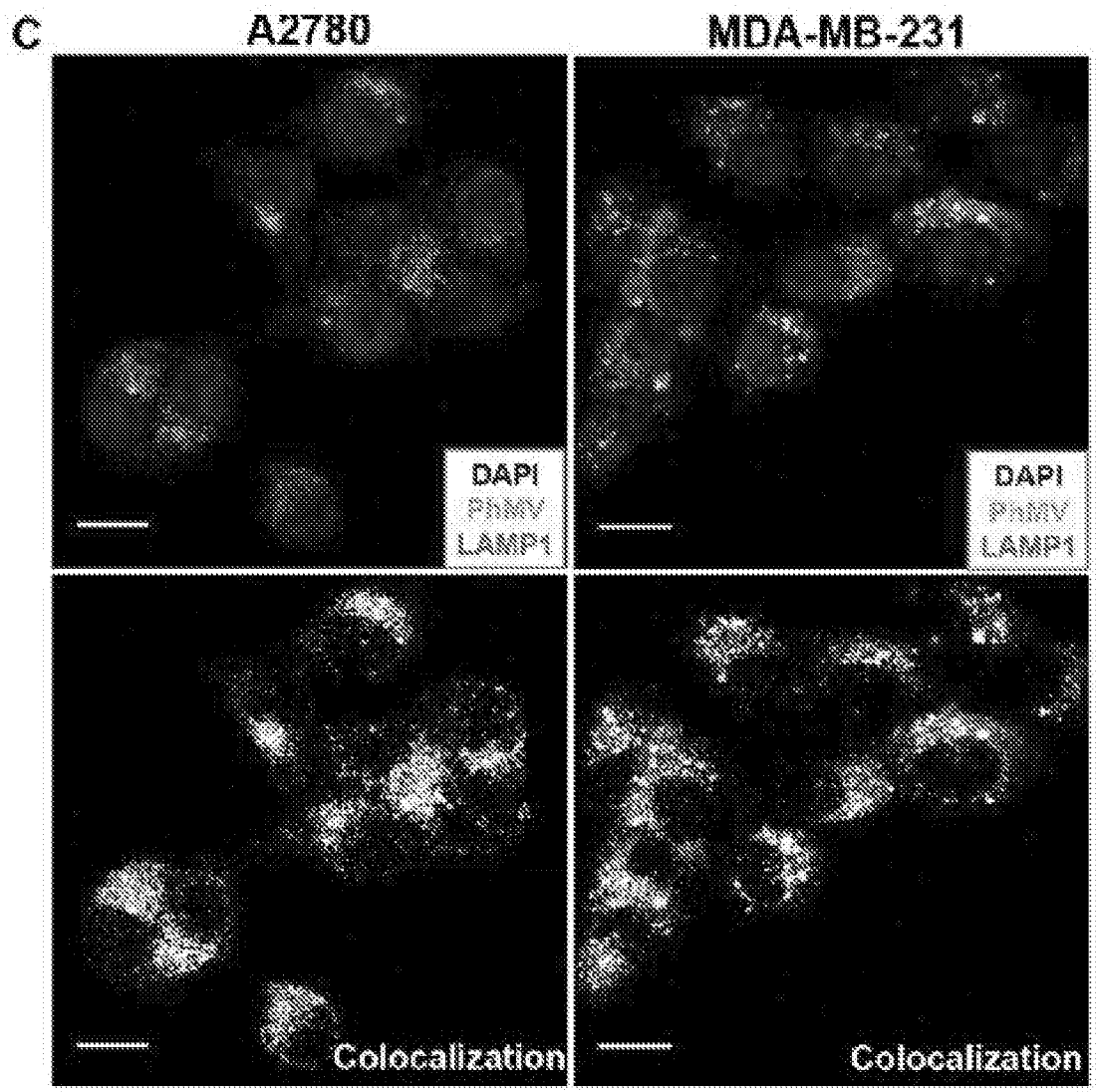
FIGS. 4(A-D) illustrate cell uptake studies with fluorescence-labeled PhMV using confocal microscopy and FACS. (A) Confocal images representing the internalization of PhMV-KE-Cy5 in A2780, MDA-MB-231 and PC-3 cells.

The avidin bead assay was used to selectively capture VLPs displaying biotin on the external surface. The avidin agarose beads were mixed with unlabeled VLPs, PhMV-$K_E$-bio particles, or PhMV-$C_I$-bio particles; the beads were washed, and the particles were eluted in agglutinin, which stains the cell membrane. The analysis of confocal images using ImageJ software confirmed the internalization of PhMV-$C_I$-Cy5.5 particles. In A2780 and MDA-MB-231 cells, we confirmed that the internalization of PhMV-$C_I$-Cy5.5 particles involved endocytosis, and the particles colocalized with the endolysosomal marker LAMP-1 (FIG. 4C).

These results indicate that PhMV-$C_I$-Cy5.5 particles are the most suitable candidates for future in vivo imaging and tumor homing studies. The efficient internalization of these particles by cancer cells (up to 100% uptake) probably reflects the retained positive surface charge (+0.38) as revealed by native gel electrophoresis (FIG. 2B, lane 3). In contrast, PhMV-$K_E$-Cy5 particles are taken up less efficiently due to the neutralization of positively charged lysine residues by NHS esterification (FIG. 2B, lower panel, lane 2), resulting in a net negative charge of −7.92 that would repel like charges on the cell membrane.

VLP Infusion and Characterization of the Loaded Particles

The potential of the VLPs to encapsulate cargo molecules was tested using the tracer dye rhodamine B, fluorescein, the cancer drug doxorubicin (DOX), the anthelmintic drug crystal violet, the photodynamic therapeutic photosensitizer (PS) cationic zinc ethynylphenyl porphyrin, and the cancer drug mitoxantrone (MTX), all of which are positively charged and fluorescent—apart from fluorescein which is neutral, allowing quantification by UV/visible spectroscopy based on absorbance.

Intact VLPs were incubated in a bathing solution containing the guest molecule at various molar excesses (500, 2500, 5000 and 10,000 molecules per VLP) in KP buffer with 10% (v/v) DMSO overnight at room temperature. After the reaction, excess guest molecules were removed by ultracentrifugation and the amount of protein and cargo was quantified by the Bradford assay and UV/visible spectroscopy, respectively. We applied the Beer-Lambert law and the specific extinction coefficient of each guest molecule to determine the number of cargo molecules per VLP (FIG. 5). The VLPs showed the greatest affinity for crystal violet (2000 molecules per particle) and the lowest affinity for rhodamine B, fluorescein, and PS (~200 molecules per particle). The VLPs showed intermediate affinities for DOX and MTX, with 750 DOX and 450 MTX molecules per particle, respectively (FIG. 5). The differences in loading probably reflect the density and distribution of charged and hydrophobic groups on the guest molecules.

The purification of the drug-loaded VLPs resulted in 50-60% recovery compared to the amount of starting material. Two formulations (PS-PhMV and DOX-PhMV) were taken forward for complete characterization and testing for in vitro cargo delivery and cell killing efficacy. We used a 5000-fold molar excess of PS or DOX per particle for further experiments because this facilitated efficient loading without significant aggregation. Extending the incubation time did not increase the loading efficiency at this molar ratio (data not shown). We consistently observed the loading of 160-180 PS molecules and 600-800 DOX molecules per VLP (FIG. 5).

Denaturing gel electrophoresis was used to confirm that PS and DOX were loaded into the cavity of the VLPs non-covalently (FIGS. 2A, B). Gels were visualized under UV light before Coomassie staining, and under white light afterwards. In denaturing gels, the PS-PhMV and DOX-PhMV coat proteins co-migrated with the native PhMV coat protein. Denaturing releases the encapsulated cargo (PS or DOX), which has a high mobility due to the low molecular weight of each molecule (PS=1130 g mol$^{-1}$, DOX=579.98 g mol$^{-1}$) resulting in a fluorescent buffer front (FIG. 2A, lanes 4 and 6). However, the DOX-PhMV coat proteins (~26 kDa) also showed evidence of fluorescence, indicating that some DOX remained associated with the protein even under denaturing conditions within the electrophoretic field (FIG. 2A, lane 6).

This may reflect hydrophobic interactions between DOX and aromatic amino acids on the VLP internal surface. Anthracycline drugs such as DOX interact with proteins such as human serum albumin and human α-1 acid glycoprotein via hydrophobic interactions that are stabilized by hydrogen bonds. We have previously proposed that DOX associates with PVX particles via hydrophobic interactions, specifically involving π-π stacking between the benzene rings of DOX and nonpolar aromatic amino acids such as phenylalanine, tyrosine and tryptophan. Likewise, DOX can also interact via π-π stacking with other DOX molecules. After Coomassie staining, the PS-PhMV and DOX-PhMV coat proteins appeared as two bands representing the monomer and a dimer, indicating some degree of aggregation (FIG. 2A, lane 4 and 6). However inter-particle aggregation was not apparent during FPLC and TEM analysis (see below).

Native agarose gel electrophoresis was used to confirm that PS and DOX were associated with the VLPs and were not free in solution. After separating the loaded particles, the gels were visualized under UV light, stained with Coomassie, and imaged under white light (FIG. 2B). Both particles showed fluorescence under UV light, indicating stable association with PS and DOX. Free drug molecules were not detected during native electrophoresis (FIG. 2B, lanes 5 and 7). In the electric field, the VLPs and both cargo molecules migrate towards the cathode because all three are positively charged (FIG. 2B, lane 4, 5 and 6, 7). Imaging the gels after Coomassie staining confirmed the presence of native PhMV, PS-PhMV and DOX-PhMV as single bands in the corresponding lanes (FIG. 2B, lane 1, 5 and 6). The co-migration of PhMV, PS-PhMV and DOX-PhMV particles indicated that the cargo molecules are encapsulated by the VLPs, although additional surface association cannot be excluded.

Size exclusion chromatography (SEC) using FPLC and a Superose-6 column showed the typical elution profiles for intact drug-loaded VLPs, consistent with the elution profile of native PhMV (FIG. 2C; bottom panel). The FPLC profiles also indicated the co-elution of PS and DOX at 450 nm and 496 nm, respectively, confirming the successful loading of these molecules. Finally, TEM analysis confirmed the integrity of the particles after loading with PS or DOX. The TEM images clearly showed that the approximately spherical structure of the wild-type particles was unchanged after loading, and there was no significant change in size from the wild-type particle diameter of 28-29 nm (FIG. 2D; bottom panel). The stability of the loaded VLPs was tested again by FPLC after storage for several weeks or months in KP buffer at 4° C. The elution profiles did not change after storage, confirming that the cargo was stably encapsulated, and there was no evidence of particle aggregation. Infusion therefore appears to be a suitable approach for the loading of cargo molecules into PhMV-based VLPs.

The Efficacy of Photodynamic Therapy Using PS-PhMV Particles Against PC3 Cells

Figure 4D:
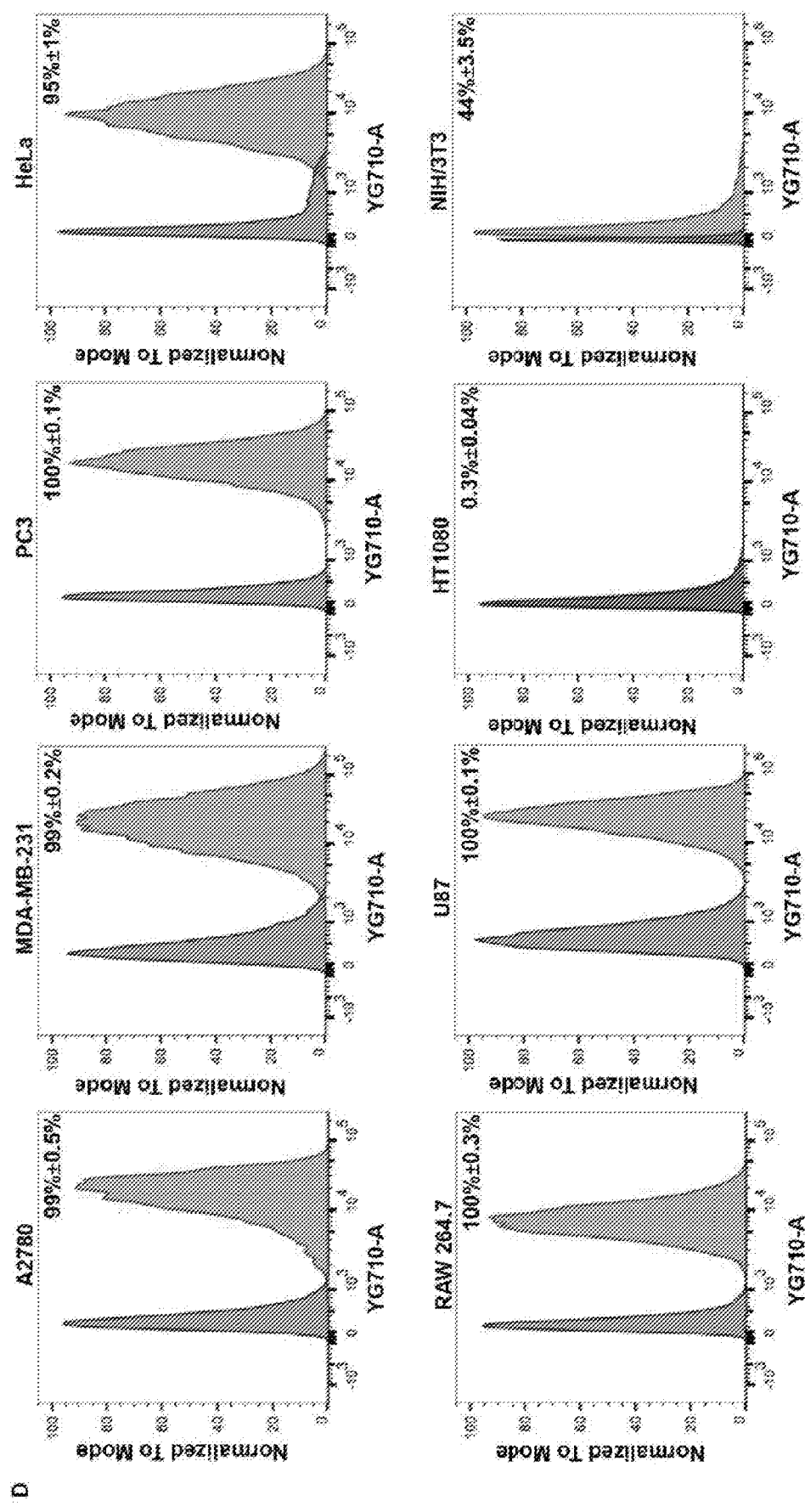
Figure 6A:
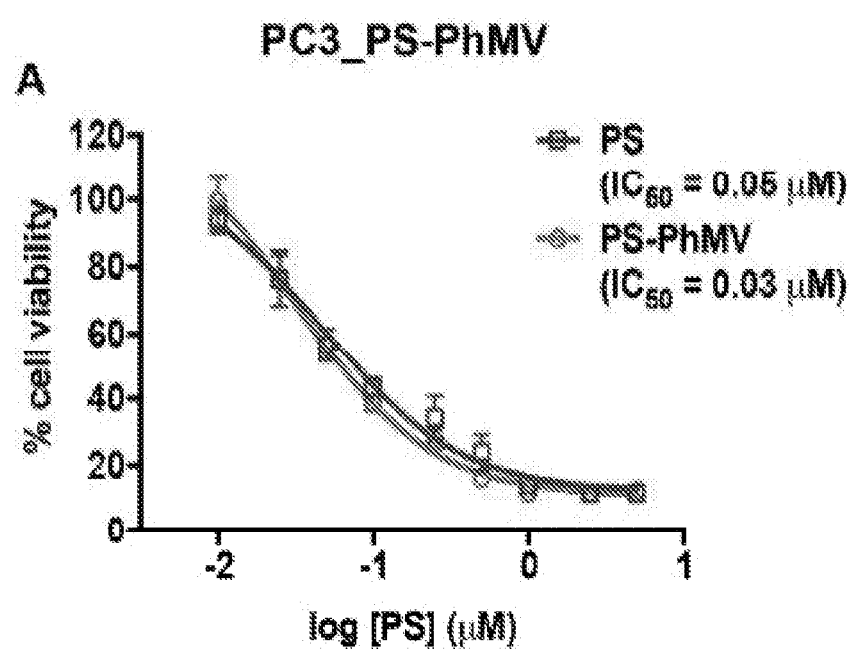
Figure 6B:
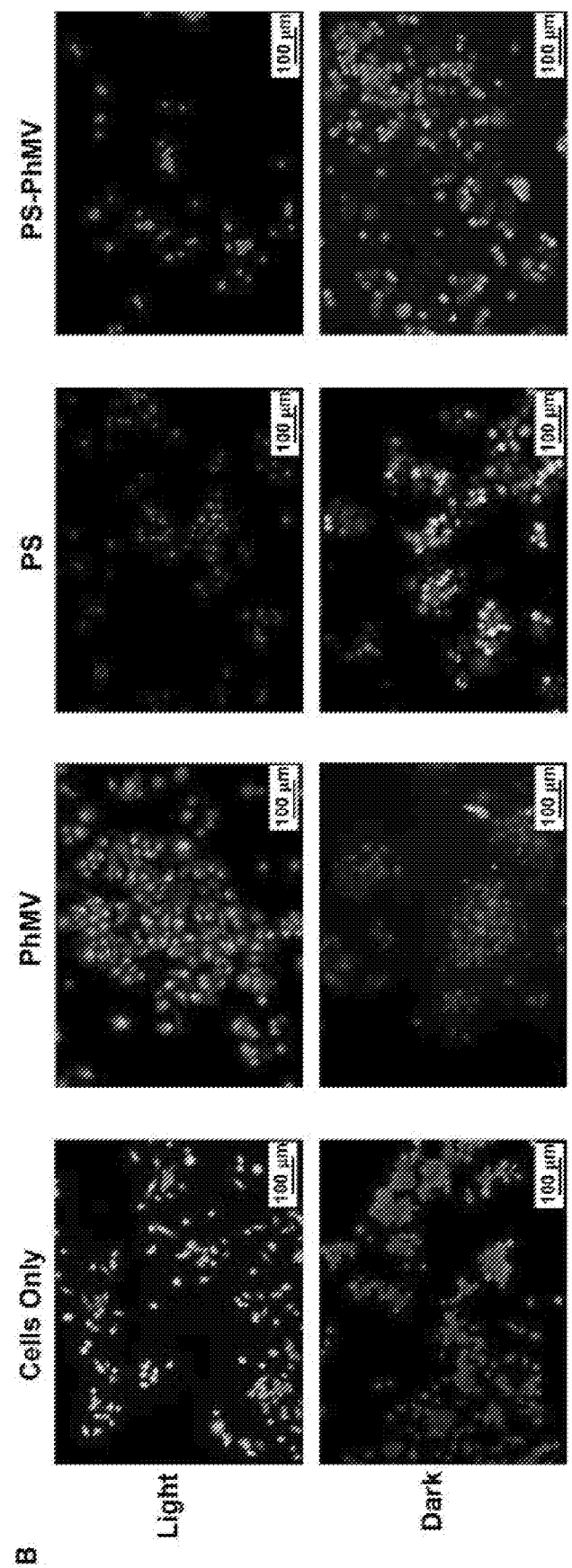
Figure 6D:
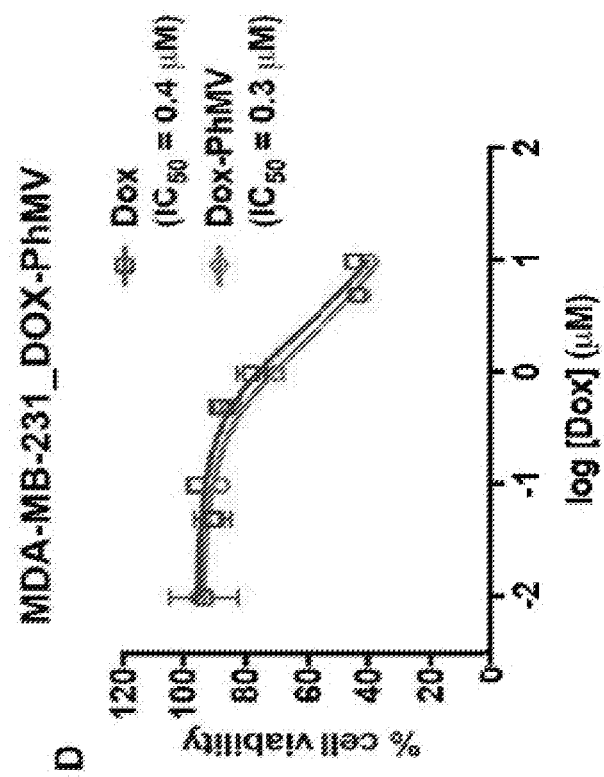

The delivery of PS-PhMV particles and their efficacy in vitro were evaluated in PC-3 cells because efficient internalization had already been demonstrated in these cells (FIG. 4D) and photodynamic therapy has a strong potential for the treatment of prostate cancer. To evaluate the efficacy of PS-PhMV compared to free PS, we incubated the cells with each reagent for 8 h, with concentrations of PS ranging from 0.01 to 5.0 PM. Treatment was induced by exposing the cells to white light, whereas controls were kept in the dark. Unloaded VLPs were used as additional controls, at the same protein concentration as the highest dose of drug-loaded particles. Cell viability was measured using an MTT assay to assess metabolic activity. We found that the efficacy of free PS ($IC_{50}$=0.05 PM) was not significantly affected by encapsulation: the $IC_{50}$ value of the PS-PhMV particles was 0.03 μM (FIG. 6A). PS-PhMV controls maintained in the dark showed no evidence of cytotoxicity, nor did the unloaded VLPs, demonstrating the biocompatibility of the PhMV platform technology. The performance of the PS-PhMV particles was confirmed by setting up a LIVE/DEAD cell viability assay in 24-well plates. As above, confluent PC3 cells were incubated for 8 h with 5.0 μM free PS or PS-PhMV (or corresponding controls), a concentration that achieved maximum cytotoxicity in the MTT assay. After removing any remaining extracellular PS/PS-PhMV, white light was applied for 30 min. The cells were incubated overnight in the dark, then stained with a combination of calcein-AM and ethidium homodimer-1 to detect living and dead cells, respectively (FIG. 6B). As above, PS and PS-PhMV controls maintained in the dark remained 100% viable, as did untreated cells ad illuminated cells exposed to unloaded VLPs. In contrast, illuminated cells exposed to 5.0 μM PS or PS-PhMV showed 0% viability.

These data are consistent with our previous reports in which CPMV or TMV were used to deliver PS. Other examples include dual-surface modified bacteriophage MS2 capsids encapsulating PS and carrying an external Jurkat-specific aptamer, resulting in the selective killing of Jurkat leukemia T cells. Similarly, the simultaneous modification of bacteriophage Qβ VLPs with a metalloporphyrin-based PS and a glycan ligand achieved the specific targeting of $CD22^+$ cells.

DOX-PhMV Delivery to Breast and Ovarian Cancer Cells

Figure 6C:
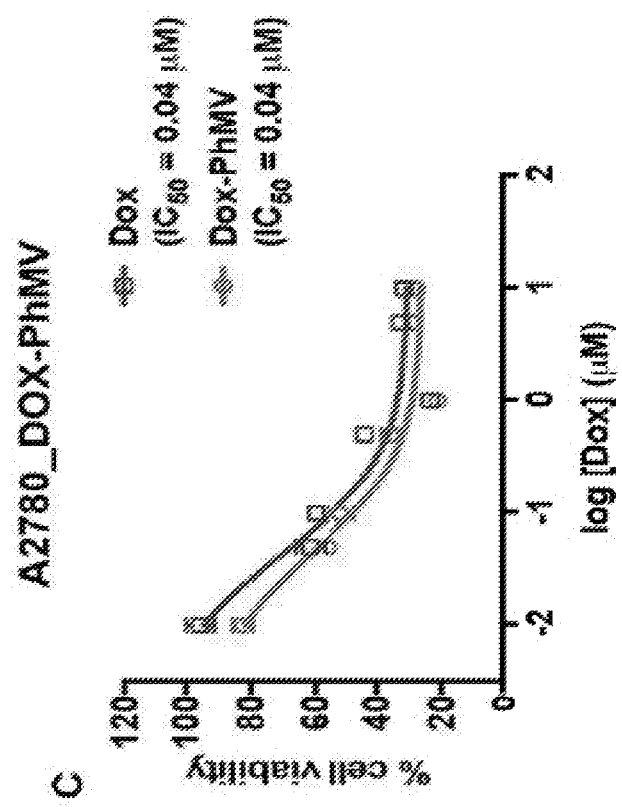

Finally, we investigated whether DOX retained its cytotoxic activity in the context of DOX-PhMV particles by exposing A2780 ovarian cancer cells and MDA-MB-231 breast cancer cells to a range of concentrations of free DOX (0.1 to 10 μM) and equivalent concentrations of DOX in the context of DOX-PhMV particles. We found that the cytotoxicity of free DOX was not significantly affected by encapsulation. The $IC_{50}$ value of the DOX-PhMV particles was 0.3 μM in the breast cancer cells and 0.04 μM in the ovarian cancer cells, equivalent to the corresponding values for the free drug (FIGS. 6C, D). In both cell lines, the unloaded VLPs showed no toxicity at the protein concentration corresponding to the highest dose of DOX-PhMV, confirming the biocompatible nature of the VLP delivery platform. Based on the cell uptake and imaging data, we propose that PhMV is taken up by endocytosis and is trafficked to the lysosome where the protein carrier is degraded thus releasing the guest molecule (DOX in this case) which diffuses into the cytosol and kills the cell.

DOX is a highly potent drug used for cancer treatment but delivery vehicles are required to overcome its dose-limiting toxicity towards healthy cells. Non-viral and viral delivery systems are undergoing pre-clinical and clinical testing. Although each carrier system has advantages and disadvantages, VLPs are robust, monodisperse, easy and inexpensive to produce, biocompatible, biodegradable and non-infectious—they are also readily engineered for the site-specific introduction of new functionalities by genetic modification or bioconjugation, which can increase their solubility, reduce their immunogenicity, allow specific cell targeting, increase the efficiency of internalization, and increase their potency. Several plant viruses have been used to encapsulate DOX by infusion though gating or simple diffusion and caging mechanisms. For example, the depletion of divalent cations ($Ca^{2+}$ and $Mg^{2+}$) induces significant conformational changes in the Red clover necrotic mosaic virus (RCNMV) capsid, leading to the reversible formation of pores that allow the ingress of dyes and DOX molecules into the internal cavity, where they bind to the negatively charged virus genome. RCNMV was thus loaded with DOX and armed with targeting peptides as a multifunctional tool to target and deliver cargo to cancer cells. Another example is encapsulated DOX nanoconjugates targeted to folate-expressing cancer cells in vivo using the Cucumber mosaic virus (CMV) platform. We have demonstrated that CPMV, PVX and TMV achieve the efficient delivery of DOX and targeted cell killing using bioconjugation and encapsulation protocols.

Whereas the reports discussed above used replication-competent viruses that retain their genomic RNA, VLP platforms lack an infectious genome and thus offer a safer alternative.

In summary, we developed bioconjugation chemistries and infusion protocols that enable the functionalization of PhMV-based VLPs, thus providing multiple approaches to modify the behavior and properties of the corresponding particles. The PhMV-derived VLPs are stable and inexpensive to produce, allowing their development as nanocarriers for in vitro drug delivery applications. The physical stability and batch-to-batch consistency are advantageous because the functionalized VLPs remain stable for long periods in storage. The production of PhMV-based VLPs could be scaled up by increasing the capacity of bacterial fermentation, but even greater scalability could be achieved by expression in plants. PhMV does not replicate in mammals, but is biocompatible and biodegradable, adding a layer of safety compared to mammalian virus-based systems.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating and/or detecting cancer tissue in a subject comprising administering to the subject a therapeutically effective amount of a plurality of functionalized Tymovirus virus or Tymovirus virus-like particles (VLPs) loaded with or conjugated to a cancer-specific targeting agent, wherein the plurality of functionalized Tymovirus virus or VLPs are loaded with one or more of an anticancer agent or an imaging agent to image the cancer tissue, and wherein the anticancer agent or imaging agent are is non-covalently encapsulated within an interior surface of the Tymovirus virus or Tymovirus VLPs.

2. The method of claim 1, wherein the Tymovirus virus belongs to the physalis mottle virus (PhMV) species.

3. The method of claim 1, wherein the Tymovirus virus or VLPs have been PEGylated.

4. The method of claim 1, wherein the Tymovirus virus or VLPs comprise an imaging agent.

5. The method of claim 4, wherein the imaging agent is a fluorescent molecule for fluorescent imaging or a chelated metal for MRI imaging.

6. The method of claim 5, wherein the Tymovirus virus or VLPs are administered at an effective amount, and further comprising the step of imaging cancer tissue in the subject using an imaging device.

7. The method of claim 1, wherein the Tymovirus virus or VLPs comprise an anticancer agent.

8. The method of claim 7, wherein the anticancer agent is an antitumor agent.

9. The method of claim 8, wherein the antitumor agent is selected from doxorubicin and mitoxantrone.

10. The method of claim 1, wherein the cancer tissue is prostate cancer, breast cancer, or ovarian cancer tissue.

11. The method of claim 1, wherein the anticancer agent is a photodynamic therapeutic (PDT) photosensitizer agent.

12. The method of claim 11, wherein the PDT agent is selected from a porphyrin and a metalloporphyrin compound.

13. The method of claim 12, wherein the porphyrin is a cationic zinc ethynylphenyl porphyrin.

14. A method of treating and/or detecting cancer tissue in a subject comprising administering to the subject a therapeutically effective amount of a plurality of functionalized Tymovirus virus or Tymovirus virus-like particles (VLPs) loaded with or conjugated to multiple cancer-specific targeting agents and one or both of an anticancer agent or an imaging agent, wherein the spacing and location of the cancer-specific targeting agents on each Tymovirus virus or VLP is controlled to facilitate delivery, targeting, and/or therapeutic efficacy of the Tymovirus virus or VLP.

15. The method of claim 14, wherein the Tymovirus virus belongs to the physalis mottle virus (PhMV) species.

16. The method of claim 14, wherein the Tymovirus virus or VLPs have been PEGylated.

17. The method of claim 14, wherein the Tymovirus virus or VLPs comprise an imaging agent.

18. The method of claim 17, wherein the imaging agent is a fluorescent molecule for fluorescent imaging or a chelated metal for MRI imaging.

19. The method of claim 18, wherein the Tymovirus virus or VLPs are administered at an effective amount, and further comprising the step of imaging cancer tissue in the subject using an imaging device.

20. The method of claim 14, wherein the Tymovirus virus or VLPs comprise an anticancer agent.

21. The method of claim 20, wherein the anticancer agent is an antitumor agent.

22. The method of claim 21, wherein the antitumor agent is selected from doxorubicin and mitoxantrone.

23. The method of claim 14, wherein the cancer tissue is prostate cancer, breast cancer, or ovarian cancer tissue.

24. The method of claim 14, wherein the anticancer agent is a photodynamic therapeutic (PDT) photosensitizer agent.

25. The method of claim 24, the PDT agent is selected from a porphyrin and a metalloporphyrin compound.

26. The method of claim 25, wherein the porphyrin is a cationic zinc ethynylphenyl porphyrin.

27. The method of claim 14, wherein the one or more of an anticancer agent, an imaging agent, or a cancer-specific targeting agent is directly conjugated to the Tymovirus virus or VLPs.

28. The method of claim 14, wherein the one or more of an anticancer agent, an imaging agent, or a cancer-specific targeting agent is conjugated to the Tymovirus virus or VLPs via a linker.

* * * * *